(12) United States Patent
Dinsmoor et al.

(10) Patent No.: US 11,896,828 B2
(45) Date of Patent: Feb. 13, 2024

(54) IMPLANTABLE LEAD LOCATION USING ECAP

(71) Applicant: Medtronic, Inc., Minneapolis, MN (US)

(72) Inventors: David A. Dinsmoor, North Oaks, MN (US); Andrew L Schmeling, Holmen, WI (US)

(73) Assignee: Medtronic, Inc., Minneapolis, MN (US)

( * ) Notice: Subject to any disclaimer, the term of this patent is extended or adjusted under 35 U.S.C. 154(b) by 102 days.

(21) Appl. No.: 17/085,621

(22) Filed: Oct. 30, 2020

(65) Prior Publication Data
US 2022/0134108 A1    May 5, 2022

(51) Int. Cl.
| | |
|---|---|
| *A61N 1/00* | (2006.01) |
| *A61N 1/36* | (2006.01) |
| *A61B 5/06* | (2006.01) |
| *A61B 5/00* | (2006.01) |
| *A61N 1/05* | (2006.01) |

(52) U.S. Cl.
CPC .......... *A61N 1/36062* (2017.08); *A61B 5/065* (2013.01); *A61B 5/686* (2013.01); *A61N 1/36128* (2013.01); *A61N 1/0551* (2013.01)

(58) Field of Classification Search
CPC .............. A61N 1/36062; A61N 1/0551; A61N 1/0553; A61N 1/36128–36164; A61B 5/065; A61B 5/686; A61B 5/06–068
See application file for complete search history.

(56) References Cited

U.S. PATENT DOCUMENTS

| | | | |
|---|---|---|---|
| 5,603,726 | A | 2/1997 | Schulman et al. |
| 5,800,465 | A | 9/1998 | Thompson et al. |
| 6,157,861 | A | 12/2000 | Faltys et al. |

(Continued)

FOREIGN PATENT DOCUMENTS

| | | |
|---|---|---|
| EP | 2396072 B1 | 3/2013 |
| WO | 2002009808 A1 | 2/2002 |

(Continued)

OTHER PUBLICATIONS

"St. Jude's Prodigy Neurostimulator with Burst Technology," Medgadget, Mar. 20, 2014, 4 pp.

(Continued)

*Primary Examiner* — Scott M. Getzow
(74) *Attorney, Agent, or Firm* — Shumaker & Sieffert, P.A.

(57) ABSTRACT

Systems, devices, methods, and techniques are described for using evoked compound action potential (ECAP) signals to determine an implant location for a lead. An example method includes receiving first information representative of a first evoked compound action potential (ECAP) signal sensed in response to a first control stimulus delivered to a first location adjacent to a spinal cord of a patient. The method also includes receiving, second information representative of a second ECAP signal in response to a second control stimulus delivered to a second location adjacent to the spinal cord of the patient. Additionally, the method includes outputting a first indication of the first information representative of the first ECAP signal and a second indication of the second information representative of the second ECAP signal.

21 Claims, 10 Drawing Sheets

(56) References Cited

U.S. PATENT DOCUMENTS

| | | |
|---|---|---|
| 6,205,360 B1 | 3/2001 | Carter |
| 6,289,247 B1 | 9/2001 | Faltys et al. |
| 6,314,325 B1 | 11/2001 | Fitz |
| 6,421,566 B1 | 7/2002 | Holsheimer |
| 6,505,078 B1 | 1/2003 | King et al. |
| 6,675,046 B2 | 1/2004 | Holsheimer |
| 6,850,802 B2 | 2/2005 | Holsheimer |
| 6,988,006 B2 | 1/2006 | King et al. |
| 7,206,640 B1 | 4/2007 | Overstreet |
| 7,333,858 B2 | 2/2008 | Killian et al. |
| 7,577,480 B2 | 8/2009 | Zeijlemaker |
| 7,616,999 B2 | 11/2009 | Overstreet et al. |
| 7,657,318 B2 | 2/2010 | King et al. |
| 7,689,289 B2 | 3/2010 | King |
| 7,742,810 B2 | 6/2010 | Moffitt et al. |
| 7,792,583 B2 | 9/2010 | Miesel et al. |
| 8,504,150 B2 | 8/2013 | Skelton |
| 8,620,441 B2 | 12/2013 | Greenberg et al. |
| 8,676,329 B2 | 3/2014 | Wacnik et al. |
| 8,694,108 B2 | 4/2014 | Alataris et al. |
| 8,708,934 B2 | 4/2014 | Skelton et al. |
| 8,712,533 B2 | 4/2014 | Alataris et al. |
| 8,712,534 B2 | 4/2014 | Wei |
| 8,897,888 B2 | 11/2014 | Parker et al. |
| 8,923,984 B2 | 12/2014 | Parker et al. |
| 9,002,460 B2 | 4/2015 | Parker |
| 9,072,910 B2 | 7/2015 | Parker et al. |
| 9,089,714 B2 | 7/2015 | Robinson |
| 9,089,715 B2 | 7/2015 | Parker et al. |
| 9,138,582 B2 | 9/2015 | Doan et al. |
| 9,155,892 B2 | 10/2015 | Parker et al. |
| 9,283,373 B2 | 3/2016 | Parker et al. |
| 9,302,112 B2 | 4/2016 | Bornzin et al. |
| 9,339,655 B2 | 5/2016 | Carbunaru |
| 9,381,356 B2 | 7/2016 | Parker et al. |
| 9,386,934 B2 | 7/2016 | Parker et al. |
| 9,387,325 B1 | 7/2016 | Min et al. |
| 9,566,439 B2 | 2/2017 | Single et al. |
| 9,597,507 B2 | 3/2017 | Johanek et al. |
| 9,700,713 B2 | 7/2017 | Robinson et al. |
| 9,764,141 B2 | 9/2017 | Moffitt et al. |
| 9,872,990 B2 | 1/2018 | Parker et al. |
| 10,183,168 B2 | 1/2019 | Baru et al. |
| 11,311,719 B2* | 4/2022 | Dubuclet ............ A61N 1/0551 |
| 2004/0267333 A1 | 12/2004 | Kronberg |
| 2005/0119713 A1 | 6/2005 | Whitehurst et al. |
| 2008/0221640 A1 | 9/2008 | Overstreet et al. |
| 2011/0054570 A1 | 3/2011 | Lane |
| 2011/0071589 A1 | 3/2011 | Starkebaum et al. |
| 2011/0077712 A1 | 3/2011 | Killian |
| 2011/0125223 A1 | 5/2011 | Carbunaru et al. |
| 2012/0155188 A1 | 6/2012 | Buettner et al. |
| 2013/0208390 A1 | 8/2013 | Singh et al. |
| 2013/0268021 A1 | 10/2013 | Moffitt |
| 2013/0289664 A1 | 10/2013 | Johanek |
| 2013/0289683 A1 | 10/2013 | Parker et al. |
| 2014/0005753 A1 | 1/2014 | Carbunaru |
| 2014/0025146 A1 | 1/2014 | Alataris et al. |
| 2014/0031896 A1 | 1/2014 | Alataris et al. |
| 2014/0031905 A1 | 1/2014 | Irazoqui et al. |
| 2014/0074189 A1 | 3/2014 | Moffitt |
| 2014/0094886 A1* | 4/2014 | Lee ................ A61N 1/36096 607/117 |
| 2014/0142656 A1 | 5/2014 | Alataris et al. |
| 2014/0142673 A1 | 5/2014 | Alataris et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243924 A1 | 8/2014 | Zhu et al. |
| 2014/0243926 A1 | 8/2014 | Carcieri et al. |
| 2014/0243931 A1 | 8/2014 | Parker et al. |
| 2014/0277282 A1 | 9/2014 | Jaax |
| 2014/0288577 A1 | 9/2014 | Robinson et al. |
| 2014/0293737 A1 | 10/2014 | Parker et al. |
| 2014/0296737 A1 | 10/2014 | Parker et al. |
| 2014/0296936 A1 | 10/2014 | Alataris et al. |
| 2014/0324143 A1 | 10/2014 | Robinson et al. |
| 2014/0371813 A1 | 12/2014 | King et al. |
| 2014/0378941 A1 | 12/2014 | Su et al. |
| 2014/0379043 A1 | 12/2014 | Howard |
| 2015/0032181 A1 | 1/2015 | Baynham et al. |
| 2015/0057729 A1 | 2/2015 | Parker et al. |
| 2015/0127062 A1 | 5/2015 | Holley et al. |
| 2015/0179177 A1 | 6/2015 | Nagao |
| 2015/0282725 A1 | 10/2015 | Single |
| 2015/0313487 A1 | 11/2015 | Single et al. |
| 2015/0360031 A1 | 12/2015 | Bomzin et al. |
| 2015/0374999 A1 | 12/2015 | Parker et al. |
| 2016/0082252 A1 | 3/2016 | Hershey et al. |
| 2016/0082268 A1 | 3/2016 | Hershey et al. |
| 2016/0121124 A1 | 5/2016 | Johanek et al. |
| 2016/0136420 A1 | 5/2016 | Brink et al. |
| 2016/0157769 A1 | 6/2016 | Min et al. |
| 2016/0158550 A1 | 6/2016 | Hou et al. |
| 2016/0166164 A1* | 6/2016 | Obradovic ........... A61B 5/7282 600/377 |
| 2016/0175594 A1 | 6/2016 | Min et al. |
| 2016/0206883 A1 | 7/2016 | Bornzin et al. |
| 2016/0287126 A1 | 10/2016 | Parker et al. |
| 2016/0287182 A1 | 10/2016 | Single |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0173332 A1 | 6/2017 | Overstreet |
| 2017/0209695 A1 | 7/2017 | Solomon |
| 2017/0216587 A1 | 8/2017 | Parker |
| 2017/0361101 A1 | 12/2017 | Single |
| 2018/0078769 A1 | 3/2018 | Dinsmoor et al. |
| 2018/0110987 A1 | 4/2018 | Parker |
| 2018/0117335 A1 | 5/2018 | Parker et al. |
| 2018/0132760 A1 | 5/2018 | Parker |
| 2018/0304075 A1* | 10/2018 | Su ................... A61N 1/36132 |
| 2019/0388692 A1 | 12/2019 | Dinsmoor et al. |
| 2019/0388695 A1 | 12/2019 | Dinsmoor et al. |
| 2020/0289815 A1 | 9/2020 | Montgomery, Jr. et al. |
| 2022/0111211 A1* | 4/2022 | Li ..................... A61B 5/366 |

FOREIGN PATENT DOCUMENTS

| | | |
|---|---|---|
| WO | 2010058178 A1 | 5/2010 |
| WO | 2012155188 A1 | 11/2012 |
| WO | 2015143509 A1 | 10/2015 |
| WO | 2015179177 A1 | 11/2015 |
| WO | 2015179281 A2 | 11/2015 |
| WO | 2016090420 A1 | 6/2016 |
| WO | 2016090436 A1 | 6/2016 |
| WO | 2016191808 A1 | 12/2016 |
| WO | 2017100866 A1 | 6/2017 |
| WO | 2017106503 A1 | 6/2017 |
| WO | 2017173493 A1 | 10/2017 |
| WO | 2017184238 A1 | 10/2017 |
| WO | 2017219096 A1 | 12/2017 |
| WO | 2018080753 A1 | 5/2018 |
| WO | 2018106813 A1 | 6/2018 |

OTHER PUBLICATIONS

Abejon MD "Back pain coverage with spinal cord stimulation: A different treatment for each patient," International Neuromodulation Society. Jun. 10, 2015; 567, Abstract Only, 1 pp.

Abeloos M. "High density stimulation as an alternative to uncomfortable cervical tonic spinal cord stimulation: case report," International Neuromodulation Society 12th World Congress, Jun. 11-15, 2015, Abstract Only, 1 pp.

Breel et al., "High Density Stimulation: A novel programming paradigm for the treatment of chronic pain," International Neuromodulation Society (INS) 12th World Congress; Jun. 9, 2015, Abstract Only, 1 pp.

Cuellar MD PhD, et al., "Effect of high-frequency alternating current on spinal afferent nociceptive transmission," Neuromodula-

(56) References Cited

OTHER PUBLICATIONS tion: Technology at the Neural Interface; Jul.-Aug. 2013; 16(4): pp. 318-327.
Cui et al., "Effect of spinal cord stimulation on tactile hypersensitivity in mononeuropathic rats is potentiated by simultaneous GABA.sub B. and adenosine receptor activation," Neuroscience Letters 247: Apr. 1998; pp. 183-186.
Cui et al., "Spinal cord stimulation attenuates augmented dorsal horn release of excitatory amino acids in mononeuropathy via a GABAergic mechanism," Pain 73, Oct. 1997, pp. 87-95.
De Ridder et al., "Burst spinal cord stimulation for limb and back pain," World neurosurgery, Nov. 2013; 80(5):642-649, e641.
De Ridder MD PhD et al., "Burst spinal cord stimulation: toward paresthesia-free pain suppression," Neurosurgery. May 2010; 66(5): 986-990.
Downey, "Asynchronous Neuromuscular Electrical Stimulation," University of Florida, 2015, accessed on Jul. 18, 2016, 107 pp.
Duyvendak MD et al., "High density stimulation: a novel programming paradigm for the treatment of chronic back and leg pain," Abstracts, International Neuromodulation Society 12th World Congress: Jun. 11-15, 2015, 1 pp.
Fern et al., "The Relationship Between Ischaemic Conduction Failure and Conduction Velocity in Cat Myelinated Axoms," Experimental Physiology, vol. 79, No. 4, Jul. 1, 1994, pp. 571-581.
Gao et al., "Effects of spinal cord stimulation with "standard clinical" and higher frequencies on peripheral blood flow in rats," Brain Res., 1313: (2010) available online Dec. 3, 2009 pp. 53-61.
GRIDER DO/PhD et al., "High Frequency (1000 Hz) Stimulation Using Commercially Available Implantable Pulse Generator," North American Neuromodulation Society. Dec. 2013, Abstract Only, 2 pp.
Guan MD PhD et al., "Spinal cord stimulation-induced analgesia: electrical stimulation of dorsal column and dorsal roots attenuates dorsal horn neuronal excitability in neuropathic rats," Anesthesiology. Dec. 2010;113(6): pp. 1392-1405.
Guan, "Spinal Cord Stimulation: Neurophysiological and Neurochemical Mechanisms of Action" Curr Pain Headache Rep DOI 10.1007s11916-014-0260-4, Mar. 8, 2012, pp. 217-225.
Holsheimer, "Computer modelling of spinal cord stimulation and its contribution to therapeutic efficacy," Spinal Cord Aug. 1998, 36: pp. 531-540.
Hubscher et al., "Convergence and cross talk in urogenital neural circuitries," J. Neurophysiol 110: 1997-2005, first published Aug. 7, 2013, 9 pp.
Hunt et al. The molecular dynamics of pain control. Nat Rev Neurosci. Feb. 2001;2(2):83-91.
Jiang et al., "Hyperexcitability in Synaptic and Firing Activities of Spinal Motoneurons in an Adult Mouse Model of Amyotrophic Lateral Sclerosis," Neuroscience, vol. 362, Oct. 24, 2017, pp. 33-46.
Kemler MD et al., "Spinal cord stimulation in patients with chronic reflex sympathetic dystrophy," N Engl J Med, Aug. 31, 2000; 343(9):pp. 618-624.
Kilgore PhD et al., "Reversible Nerve Conduction Block Using Kilohertz Frequency Alternating Current," Neuromodulation. Aug. 2013, pp. 242-255.
Kumar et al., "Spinal cord stimulation versus conventional medical management for neuropathic pain: a multicentre randomised controlled trial in patients with failed back surgery syndrome," Pain Jul. 2007; 132(1-2): 179-188.
Likar et al., "High density spinal cord stimulation: a multi-center experience," Abstracts, International Neuromodulation Society 12th World Congress; Jun. 11-15, 2015, 1 pp.
Maeda et al., "Increased c-fos immunoreactivity in the spinal cord and brain following spinal cord stimulation is frequency-dependent," Brain Res. Mar. 9, 2009;1259: pp. 40-50, available online Jan. 6, 2009.
Maeda et al., "Low frequencies, but not high frequencies of bi-polar spinal cord stimulation reduce cutaneous and muscle hyperalgesia induced by nerve injury," Pain; Feb. 2008; 138(1): pp. 143-152.

Maggi et al., "Effect of urethane anesthesia on the micturition reflex in capsaicin-treated rats." Journal of the Autonomic Nervous System, Jan. 1990, 30(3): 247-251.
Matsuka et al., "Hyperosmolar Solutions Selectively Block Action Potentials in Rat Myelinated Sensory Fibers: Implications for Diabetic Neuropathy," Journal of Neurophysiology, vol. 91, No. 1, Sep. 17, 2003, pp. 48-56.
Nicholls et al., "Reflexes, Fictive Respiration and Cell Division in the Brain and Spinal Cord of the Newborn Opossum, Monodelphis Domestica, Isolated and Maintained in Vitro," Journal of Experimental Biology, vol. 152, May 4, 1990, 17 pp.
North MD et al., "Clinical outcomes of 1 kHz subperception spinal cord stimulation (SCS): Results of a prospective randomized controlled crossover trial," Abstracts, International Neuromodulation Society, Jun. 2015, 1 pp.
North MD et al., "Spinal cord stimulation versus repeated lumbosacral spine surgery for chronic pain: a randomized, controlled trial," Neurosurgery, Jan. 2005; 56(1): 98-106; discussion 106-107.
Nussbaumer et al., "Pharmacological properties of a C-Fibre Response Evoked by Saphenous Nerve Stimulation in an Isolated Spinal Cord-Nerve Preparation of the Newborn Rat," British Journal of Pharmacology, vol. 98, No. 2, Oct. 1989, pp. 373-382.
Ranck Jr. et al., "Which elements are excited in electrical stimulation of mammalian central nervous system: a review," Brain Research, Nov. 21, 1975; 98(3): pp. 417-440.
Replogle MD. et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
Sato et al., "Spinal cord stimulation reduces hypersensitivity through activation of opioid receptors in a frequency-dependent manner," Eur J Pain. Apr. 2013 (4): pp. 551-561, first published Oct. 5, 2012.
Schu MD, PhD. et al., "A prospective, randomised, double-blind, placebo-controlled study to examine the effectiveness of burst spinal cord stimulation patterns for the treatment of failed back surgery syndrome," Neuromodulation. Apr. 2014; 17(5): pp. 443-450.
Shechter MD et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.
Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.
Smith et al., "Successful use of high-frequency spinal cord stimulation following traditional treatment failure," Stereotact Funct Neurosurg. Apr. 1, 2015; 93(3): pp. 190-193.
Snellings et al., "Effects of stimulation site and stimulation parameters on bladder inhibition by electrical nerve stimulation," BJU International, Jul. 2012, pp. 136-143, first published Jan. 19, 2012.
Song MD Phd. et al., "Efficacy of kilohertz-frequency and conventional spinal cord stimulation in rat models of different pain conditions, " Neuromodulation Jan. 2014; 17(3): pp. 226-234.
Sweet MD et al., "High Frequency vs. Burst Stimulation Patterns for Dorsal Column Stimulation: The Importance of Charge," American Association of Neurological Surgeons, Abstract, Apr. 4, 2014, 2 pp.
Walter et al., "Inhibiting the hyperreflexic bladder with electrical stimulation in a spinal animal model." Neurourology and Urodynamics, 1993, 12:241-253. doi:10.1002/nau.1930120306. Applicant points out in accordance with MPEP 609.04(a) that the 1993 year of publication is sufficiently earlier than the effective U.S. filing date of the present application, and any foreign priority date that the particular month of publication is not in issue.
Wille MD et al., "Altering Conventional to High Density Spinal Cord Stimulation: An Energy Dose-Response Relationship in Neuropathic Pain Therapy," Neuromodulation 2016, Aug. 2016, 9 pp.

(56) References Cited

OTHER PUBLICATIONS

Woock et al., "Activation and inhibition of the micturition reflex by penile afferents in the cat," Am J. Physiol Regul Intergre Comp Physiol, published Apr. 23, 2008, pp. R1880-R1889.
Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
Extended Search Report from counterpart European Application No. 21201439.3, dated Mar. 23, 2022, 9 pp.
Response to Extended Search Report dated Mar. 23, 2022, from counterpart European Application No. 21201439.3, filed Oct. 24, 2022, 5 pp.

\* cited by examiner

US 11,896,828 B2

IMPLANTABLE LEAD LOCATION USING ECAP

TECHNICAL FIELD

This disclosure generally relates to medical devices, and more specifically, device and techniques for determining a position of implanted electrodes.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively. Electrical stimulation may be delivered to a patient by the medical device in a train of electrical pulses, and parameters of the electrical pulses may include a frequency, an amplitude, a pulse width, and a pulse shape. An evoked compound action potential (ECAP) is synchronous firing of a population of neurons which occurs in response to the application of a stimulus including, in some cases, an electrical stimulus by a medical device.

SUMMARY

In general, systems, devices, and techniques are described for determining a position of a lead based on evoked compound action potential (ECAP) signals during interoperative placement of the lead. During placement of some leads near the spinal cord, a surgeon may prefer direct visualization of the dura via a laminectomy. However, since patients are generally under general anesthesia during the laminectomy procedure, the patient cannot provide any feedback to the physician about effectiveness of stimulation (e.g., laterality, location, and/or paresthesia with stimulation, etc.).

A described herein, an implantable medical device (IMD) or other system or device may determine a position of the stimulating and/or sensing electrodes of the lead with respect to the spinal cord based on ECAP signal characteristics. For patients, a position directly over the dorsal side of spinal column may result in optimal therapeutic outcomes with spinal cord stimulation, although other positions with respect to the spinal column may be preferred in other examples. To determine a placement location of the lead, after visualization of the dura via laminectomy, the lead is placed (e.g., by a surgeon, by remote instrument control with haptic feedback, etc.) laterally on either side of the anatomical midline of the dorsal side of the spinal column. The lead is then incrementally moved (e.g., rotated or moved laterally) from one side of midline towards the other side while simultaneously providing stimuli and recording the respective resulting ECAP signals to establish the ECAP characteristics at each location. This process may be repeated as needed to establish the characteristics of ECAP signals multiple locations until the desired location is identified. Based on the characteristics of ECAP signals, the system or physician may select the desired lead placement location. For example, the location may be based on a specific ECAP characteristic, such as particular ECAP amplitude or area under the curve (e.g., an ECAP of 120 µV, etc.). As another example, the location may be based on offset from a certain point, such a 2 mm medial placement from the point where a 50 µV ECAP is measured. The lead is placed at the selected placement location (e.g., fixating the lead with sutures or equivalent, etc.). This procedure can provide a higher degree of confidence in a lead placement that will provide effective therapeutic outcomes even when the patient is under general anesthesia and cannot provide feedback about delivered stimulation.

In one example, a system includes stimulation circuitry configured to generate electrical stimulation deliverable via an electrode combination of an electrode array, sensing circuitry configured to sense an evoked compound action potential (ECAP) signal, and processing circuitry. The processing circuitry controls the stimulation circuitry to deliver a first control stimulus to the electrode combination of the electrode array positioned at a first location adjacent to a spinal cord of a patient. The processing circuitry also receives, from the sensing circuitry, first information representative of a first ECAP signal sensed in response to the first control stimulus. Additionally, the processing circuitry controls the stimulation circuitry to deliver a second control stimulus to the electrode combination of the electrode array positioned at a second location adjacent to the spinal cord of the patient. The processing circuitry receives, from the sensing circuitry, second information representative of a second ECAP signal in response to the second control stimulus. The processing circuitry outputs a first indication of the first information representative of the first ECAP signal and a second indication of the second information representative of the second ECAP signal.

In another example, a method includes receiving first information representative of a first evoked compound action potential (ECAP) signal sensed in response to a first control stimulus delivered to a first location adjacent to a spinal cord of a patient. The method also includes receiving, second information representative of a second ECAP signal in response to a second control stimulus delivered to a second location adjacent to the spinal cord of the patient. Additionally, the method includes outputting a first indication of the first information representative of the first ECAP signal and a second indication of the second information representative of the second ECAP signal.

In another example, a computer readable medium comprises instructions that, when executed, cause processing circuitry to receive a first input that an electrode array has been positioned in a first location adjacent to a spinal cord of a patient, control stimulation circuitry to deliver a first control stimulus to an electrode combination of the electrode array, and receive, from the sensing circuitry, first information representative of a first evoked compound action potential (ECAP) signal sensed in response to the first control stimulus. The instructions also cause the processing circuitry to receive a second input that the electrode array has moved from the first location to a second location adjacent to the spinal cord of the patient, control the stimulation circuitry to deliver a second control stimulus to the electrode combination of the electrode array positioned at the second location, and receive, from the sensing circuitry, second information representative of a second ECAP signal in response to the second control stimulus. Additionally, the instructions cause the processing circuitry to output a first indication of the first information representative of the first ECAP signal and a second indication of the second information representative of the second ECAP signal.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
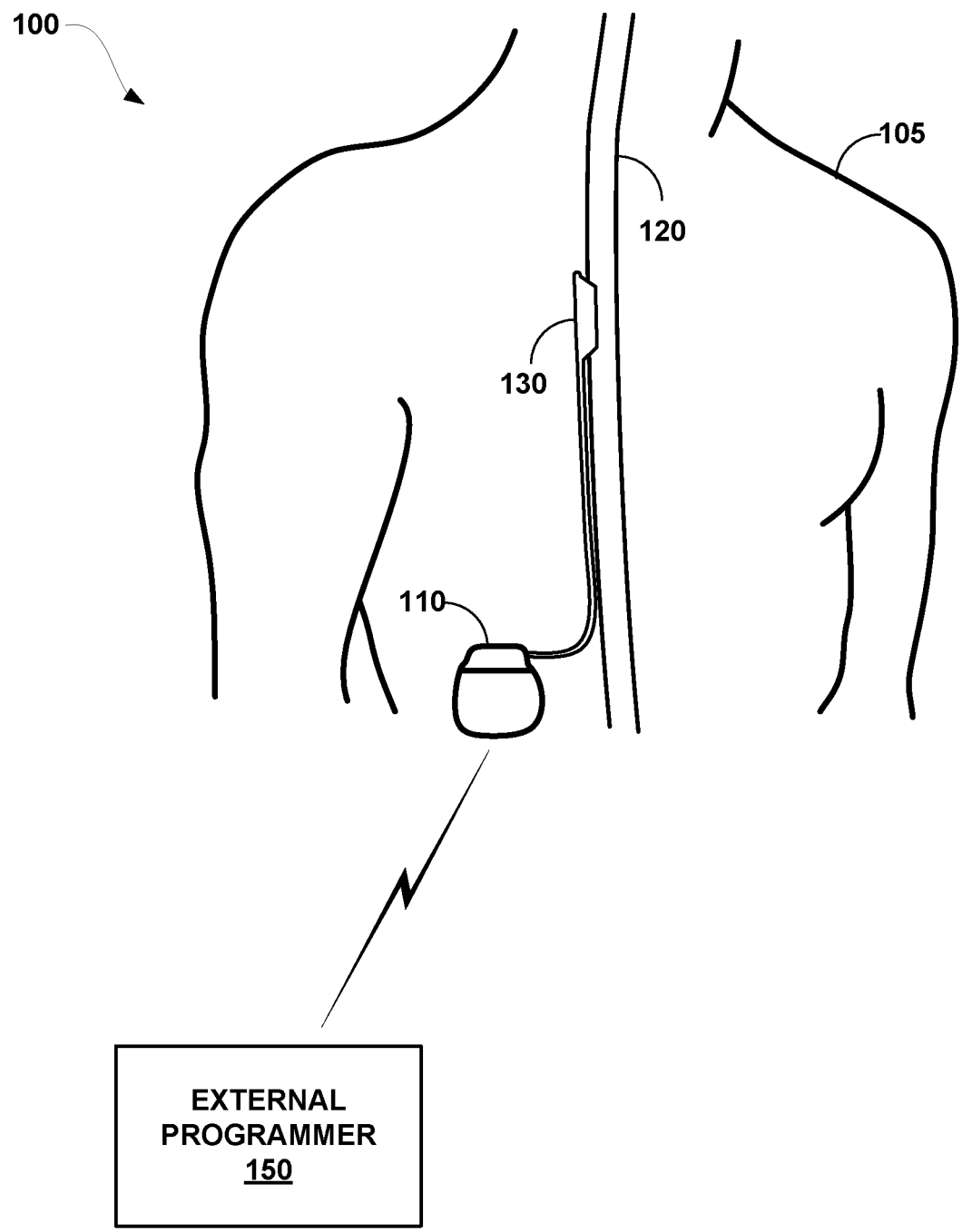
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes examples of medical devices, systems, and techniques to position a lead based on one or more characteristics of evoked compound action potentials (ECAPs). Electrical stimulation therapy is typically delivered to a target tissue (e.g., nerves of the spinal cord or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, nervous system disorders, muscle disorders, etc. Electrodes implanted in a patient are positioned to provide effective therapy based on the stimulation parameters. For placement of some leads, such as percutaneous leads, a patient may be placed under monitored anesthesia care. As such, a patient may be awoken to provide feedback regarding placement of the lead (e.g., provide feedback of the therapeutic effect of stimulation provides at different locations). However, there are some risks with monitored anesthesia care (e.g., airway compromise and/or incomplete sedation, etc.), and some patients may prefer and/or be more suitable for general anesthesia. Additionally, during the placement of some leads, such as paddle leads, placement may require direct visualization of the dura of the spinal cord which often requires removal or modification of bone (e.g., via a laminectomy) that requires more invasive surgery than percutaneous placement. Because a laminectomy can be painful, a patient is generally placed under general anesthesia and therefore cannot be awoken to provide feedback during the procedure. Further, in general, the target location—i.e., the midline of the dorsal columns—is not easy to locate for lead placement based exclusively on a visual inspection.

ECAPs are a measure of neural recruitment because each ECAP signal represents the superposition of electrical potentials generated from a population of axons firing in response to an electrical stimulus (e.g., a stimulation pulse). The ECAP may be detectable as being a separate event from the stimulus itself, and the ECAP may reveal characteristics of the effect of the stimulus on the nerve fibers. That is, changes in a characteristic (e.g., an amplitude of a portion of the signal, peak-to-peak voltage of the signal, or area under the curve of the signal, etc.) of an ECAP signals occur as a function of how many axons have been activated by the delivered stimulation pulse. For a given set of parameter values that define the stimulation pulse and a given distance between the electrodes and target nerve, the detected ECAP signal may have a certain characteristic value (e.g., amplitude). In some examples, changes in the latency between when the stimulus is delivered and when the ECAP is detected are used to assess placement of the lead. For example, ECAP signals with lower latency (i.e., smaller latency values) indicate a higher percentage of nerve fibers that have faster propagation of signals (e.g., the stimulus is located closer to the target location, etc.), whereas ECAP signals with higher latency (i.e., larger latency values) indicate a higher percentage of nerve fibers that have slower propagation of signals (e.g., the stimulus location is farther from the target location, etc.).

As described herein, systems, devices, and techniques are described for interoperative placement of one or more leads for an implantable medical device (IMD). Techniques described herein may be used when, for example, a patient is not be able to provide feedback or provide an initial starting point from which a patient may then provide feedback, etc. To determine a placement location of the lead, after visualization of the dura via laminectomy, the lead is placed (e.g., by a surgeon, by remote instrument control with haptic feedback, etc.) laterally on either side of the anatomical midline of the dura and spinal cord. The lead is then incrementally or continuously moved laterally from one side of midline to the other while the system simultaneously provides stimuli and recording of the respective resulting ECAP signals to establish the ECAP characteristics at each position. For example, the lead may be moved laterally in 1 mm increments, with ECAP recordings taken at each location. This may be repeated to establish the characteristics of ECAP signals at each location. Based on the characteristics of ECAP signals, a lead placement location is selected. For example, the placement may be based on a specific ECAP characteristic, such as the location with the maximum peak-to-peak voltage and/or the location with the lowest latency, etc. The lead is placed at the selected placement location (e.g., fixating the lead with sutures or equivalent, etc.). The system may automatically select the appropriate position or provide the physician with information derived from the ECAP characteristics in order to enable the physician to select the desired location based on the characteristics of the ECAP signals.

Different leads may benefit from different placement strategies. Leads may be omnidirectional leads with a single row of ring electrodes that a capable of providing stimulation and sensing ECAP signals in directions around the lead. In other examples, leads may be shielded paddle leads that include one or more rows of electrodes that provide stimulation and sense ECAP signals in a single direction (e.g., in the direction facing the spinal cord). In some examples, when a lead has a single row or odd number of rows of electrodes, a set of electrodes in a central row (or only row) is used to provide stimulus and a set of electrodes in a central row (or only row) is used to sense the resulting ECAP signals. In such examples, the central row (or only row) is positioned over the target axis based on the characteristics of the ECAP signals. In some examples, when a lead has an even number of rows, electrodes in one row may be used to provide stimulus and sense the resultant ECAP signals and the lead is placed based on an offset between the center of the lead and the row of electrodes used to provide stimulus. In some examples, when a lead has an even number of rows, electrodes in two central rows may be used to provide stimulus and sense the resultant ECAP signals and the lead may be place at a location at which ECAP signals of electrodes in each of the rows are indicative that the target location is in between the rows of electrodes.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating an example system 100 that includes an implantable medical device (IMD) 110 configured to deliver spinal cord stimulation (SCS) therapy and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in the example of FIG. 1, system 100 includes an IMD 110, lead 130, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of lead 130, e.g., for relief of chronic pain or other symptoms. In the illustrated example, lead 130 is be a paddle lead. Alternatively, in some examples, lead 130 may be multiple omnidirectional leads. In some examples, the stimulation signals, or pulses, may be configured to elicit detectable ECAP signals that IMD 110 may use to determine whether lead 130 are adjacent to a target lateral axis parallel to a dorsal of spinal cord 120 while the leads are being implanted (e.g., intraoperatively, etc.). IMD 110 may be coupled to a single lead carrying multiple electrodes or more than two leads each carrying multiple electrodes. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be generated by constant current or constant voltage-based systems, for example, is delivered from IMD 110 to one or more target tissue sites of patient 105 via one or more electrodes (not shown) of implantable lead 130. In the example of FIG. 1, lead 130 carries electrodes that are placed adjacent to the target tissue (e.g., tissue parallel to a dorsal) of spinal cord 120. One or more of the electrodes may be at positions at intermediate points along the lead in one or more rows. Lead 130 may be implanted and coupled to IMD 110. The electrodes may transfer electrical stimulation generated by an electrical stimulation generator in IMD 110 to tissue of patient 105. Although lead 130 may be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead, two leads, or more than two leads, each coupled to IMD 110 and directed to similar or different target tissue sites. Therefore, the placement techniques described herein may be applied to positioning multiple leads for the same patient.

The electrodes of lead 130 may be electrode pads on a paddle lead, circular (e.g., ring) electrodes surrounding the body of the lead (e.g., an omnidirectional lead), conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. The deployment of electrodes via lead 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, lead 130 is a linear lead having multiple ring electrodes along the axial length of the lead. In another example, the electrodes are segmented rings arranged in a linear fashion along the axial length of the lead and at the periphery of the lead.

The stimulation parameter set of a therapy stimulation program that defines the stimulation pulses of electrical stimulation therapy by IMD 110 through the electrodes of lead 130 may include information identifying which electrodes have been selected for delivery of stimulation according to a stimulation program, the polarities of the selected electrodes, i.e., the electrode combination for the program, voltage or current amplitude, pulse frequency, pulse width, pulse shape of stimulation delivered by the electrodes. These stimulation parameters values that make up the stimulation parameter set that defines pulses may be predetermined parameter values defined by a user and/or automatically determined by system 100 based on one or more factors or user input.

In some examples, IMD 110 may deliver stimulation pulses that may or may not contribute to therapy perceived by patient 105. IMD 110 may detect ECAP signals elicited by these stimulation pulses. In other examples, stimulation pulses configured to provide therapy may prevent IMD 110 from detecting ECAP signals (e.g., because the pulse width of the stimulation pulses are long enough to interfere with propagating ECAP signals. Therefore, if control pulses (e.g., pulses that may or may not contribute to therapy) separate from the informed pulses configured to provide therapy are needed to elicit a detectable ECAP signal, system 100 may employ an ECAP test stimulation program that defines stimulation parameter values that define control pulses delivered by IMD 110 through at least some of the electrodes of lead 130. These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each ECAP test stimulation program are configured to evoke a compound action potential from nerves. In some examples, the ECAP test stimulation program defines when the control pulses are to be delivered to the patient based on the frequency and/or pulse width of the informed pulses. The stimulation defined by each ECAP test stimulation program may not be intended to provide or contribute to therapy for the patient, but the patient may perceive the control pulses in some examples. In addition, the ECAP test stimulation program may define the control pulses used for each sweep of pulses that are used to detect a change in an ECAP signal that is indicative of the associated lead having migrated from its original position.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by lead 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Lead 130 may be introduced adjacent to spinal cord 120 in via any suitable region, such as the thoracic, cervical, or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which causes a tingling sensation that may reduce the perception of pain by patient 105, and thus, provide efficacious therapy results.

IMD 110 is configured to generate and deliver electrical stimulation therapy to a target stimulation site within patient 105 via the electrodes of lead 130 to patient 105 according to one or more therapy stimulation programs. A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program.

Furthermore, IMD 110 may be configured to deliver control stimulation to patient 105 via a combination of electrodes of lead 130, alone or in combination with an electrode carried by or defined by an outer housing of IMD 110 in order to detect ECAP signals (e.g., via control pulses). The tissue targeted by the control stimulation may be the same or similar tissue targeted by the electrical stimulation therapy. IMD 110 may deliver control stimulation pulses for ECAP signal detection via the same, at least some of the same, or different electrodes. Like the electrical stimulation therapy, the control stimulation may be in the form of electrical stimulation pulses or continuous waveforms. In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on lead 130. In cases where the control stimulation pulses are applied to spinal cord 120, the signal may be sensed by IMD 110 from spinal cord 120.

IMD 110 can deliver control stimulation to a target stimulation site within patient 105 via the electrodes of lead 130 according to one or more ECAP test stimulation programs. The one or more ECAP test stimulation programs may be stored in a storage device of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples timing based on informed pulses to be delivered to patient 105.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control stimulation, such as electrical stimulation therapy (e.g., informed pulses) and/or control stimulation (e.g., control pulses). For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

Information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on lead 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

As described below, IMD 110 may be configured to provide control stimuli to elicit ECAP signals when lead 130 is being implanted by a surgeon. When entering a locator mode, IMD 110 provides control stimulus to certain electrodes of lead 130 and senses the resultant ECAP signals. Information representative of the ECAP signals (e.g., characteristics of the ECAP or full ECAP signals) may be transmitted to external programmer 150 to be displayed to, for example, the surgeon implanting the lead. In some examples, IMD 110 may control stimulus in response to receiving a signal that lead 130 has been moved to the initial and/or next position. IMD 110 may store the ECAP signals to be analyzed to determine which position is adjacent to the lateral axis of the target tissue. In some examples, in response to an indication that the sample ECAP signals have been captured, IMD 110 may determine which ECAP signal is indicative of lead 130 being adjacent to the target tissue based on one or more characteristics of the ECAP signals.

While the techniques to intraoperatively determine a location of lead 130 are described herein in connection with IMD 110, these techniques may be used with an external device that connects with lead 130. For example, lead 130 may be connected to a trial stimulator, such as an external neurostimulator (ENS). Lead 130 may be connected to the trial stimulator via a percutaneous connection with or without tunneling under tissue. This external device may deliver stimulation to produce the ECAP, sense the ECAP, and output information positioning information as described herein. For example, this external device may be external programmer 150 in other examples. After successful trial of stimulation, the clinician may tunnel the proximal end of lead 130 to a device pocket where the lead 130 is then attached to the IMD 110 located in the device pocket for chronic stimulation.

Figure 2:
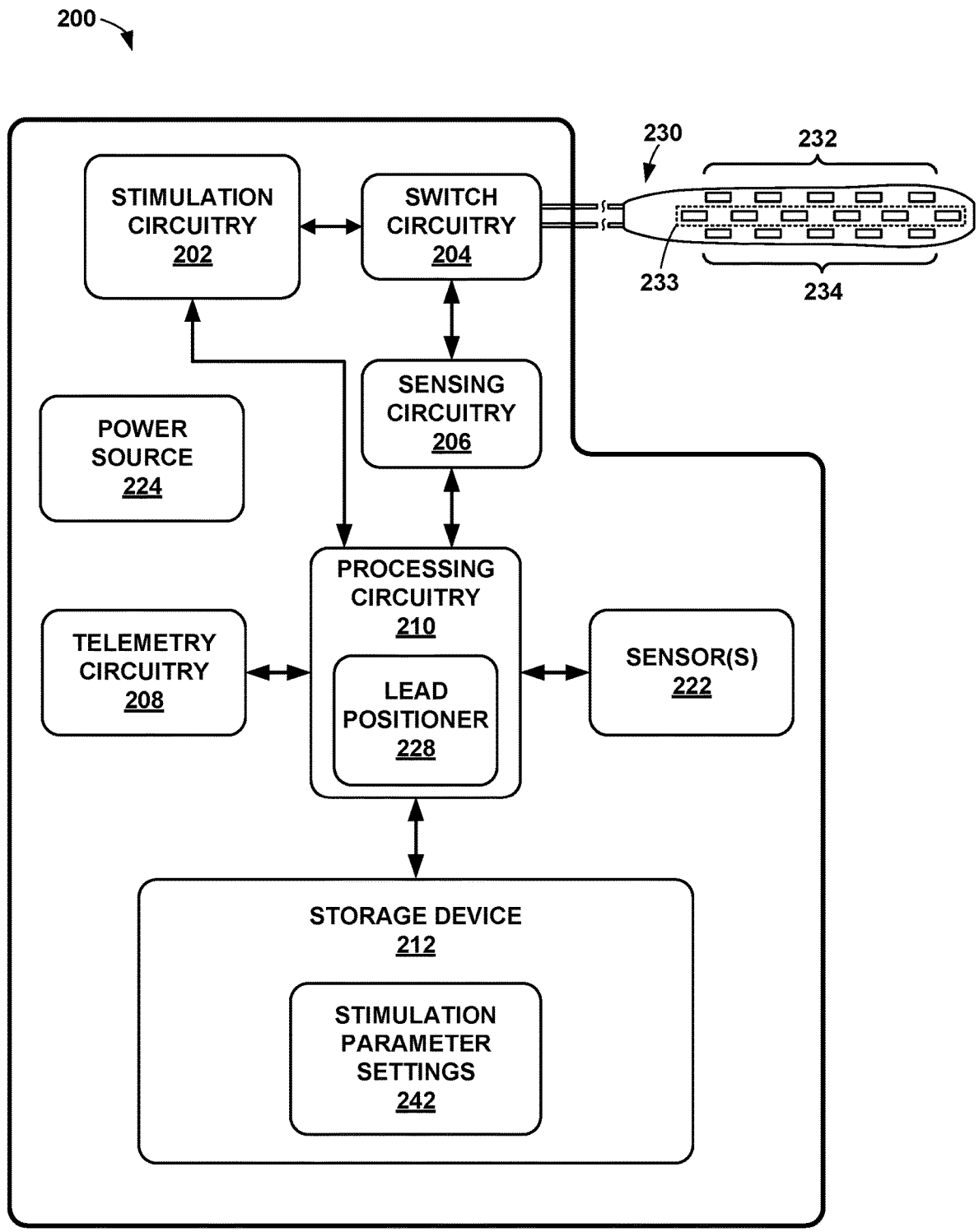
FIG. 2 is a block diagram illustrating an example configuration of components of an implantable medical device (IMD), in accordance with one or more techniques of this disclosure.

FIG. 2 is a block diagram illustrating an example configuration of components of an IMD 200, in accordance with one or more techniques of this disclosure. IMD 200 may be an example of IMD 110 of FIG. 1. Alternatively, the techniques described herein may be used in conjunction with an external device like IMD 200 that provides stimulus, senses ECAPs, and determines location for one or more leads. In the example shown in FIG. 2, IMD 200 includes stimulation generation circuitry 202, switch circuitry 204, sensing circuitry 206, telemetry circuitry 208, processing circuitry 210, storage device 212, sensor(s) 222, and power source 224.

In the example shown in FIG. 2, storage device 212 stores stimulation parameter settings 242 in separate memories within storage device 212 or separate areas within storage device 212. In some examples, stimulation parameter settings 242 may include stimulation parameter values (sometimes referred to as "sets of therapy parameters") for respective different stimulation programs selectable by the clinician or patient for therapy. In this manner, each stored therapy stimulation program, or set of stimulation parameter values, of stimulation parameter settings 242 defines values for a set of electrical stimulation parameters (e.g., a stimulation parameter set), such as a stimulation electrode combination, electrode polarity, current or voltage amplitude, pulse width, pulse rate, and pulse shape. In some examples, stimulation parameter settings 242 may store a primary set of therapy parameters for when lead 230 is in an implant location and a secondary set of therapy parameters for when lead 230 has temporarily (e.g., due to posture, etc.) or permanently (e.g., due to lead migration, etc.) moved from the. Storage device 212 may also store ECAP test stimulation programs, as part of stimulation parameter settings 242 or as a separate memory area, that defines values for a set of electrical stimulation parameters (e.g., a control stimulation parameter set) configured to elicit a detectable ECAP signal, such as a stimulation electrode combination, electrode polarity, current or voltage amplitude, pulse width, pulse rate, and pulse shape. ECAP test stimulation programs may also have additional information such as instructions regarding when to deliver control pulses based on the pulse width and/or frequency of the informed pulses defined in stimulation parameter settings 242.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 233, 234, or directed sensed signals from one or more of electrodes 232, 233, 234 to sensing circuitry 206. In other examples, stimulation generation circuitry 202 and/or sensing circuitry 206 may include sensing circuitry to direct signals to and/or from one or more of electrodes 232, 233, 234, which may or may not also include switch circuitry 204. Electrodes 233 may include one column of electrodes at the center of lead 230, and electrodes 232 and 234 may be respective columns on either side, or laterally, of electrodes 233. In other examples, lead 203 may include one column, two columns, or more than 3 columns of electrodes.

Sensing circuitry 206 is configured to monitor signals from any combination of electrodes 232, 233, 234. In some examples, sensing circuitry 206 includes one or more amplifiers, filters, and analog-to-digital converters. Sensing circuitry 206 may be used to sense physiological signals, such as ECAP signals. In some examples, sensing circuitry 206 detects ECAPs from a particular combination of electrodes 232, 233, 234. In some cases, the particular combination of electrodes for sensing ECAPs includes different electrodes than a set of electrodes 232, 233, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via telemetry circuitry 208. Processing circuitry 210 may store updates to the stimulation parameter settings 242 or any other data in storage device 212. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 2) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to stimulation parameter settings 242 and any other instructions stored in storage device 212 to apply stimulation parameter values specified by one or more of programs, such as amplitude, pulse width, pulse rate, and pulse shape of each of the stimulation signals. In the illustrated example, processing circuitry includes lead positioner 228. Lead positioner 228 is a structure to cause IMD 110 to enter a locator mode to facilitate positioning of lead 230 without feedback from the patient. Lead positioner 228 provides control stimulus and recording the resulting ECAP signal to establish the ECAP characteristics for lead 230 at each position as lead 230 is moved laterally across spinal column 120. Lead positioner 228 provides the ECAP signals to telemetry circuitry 208 to provide a visualization (e.g., on external programmer 150) of the ECAP signal to facilitate positioning of lead 230. In some examples, lead positioner 228 may perform some post processing to identify one or more characteristics of the ECAP signals that may be indicative of when lead 230 is adjacent to the target tissue. In some examples, lead positioner 228 may provide control stimulus to certain electrodes 232 and sense the resulting ECAP signal using certain electrodes 232 based on characteristics of lead 230 (e.g., position and/or arrangement of electrodes 232, etc.). In some examples, lead positioner 228 may provide control stimulus and sense the resulting ECAP signal in response to receiving (e.g., via telemetry circuitry, etc.) an indication that lead 230 has been move to the initial position and/or the next position to be measured.

In the example shown in FIG. 2, the set of electrodes 232 includes five electrodes, set of electrodes 233 includes six electrodes, and the set of electrodes 234 includes five electrodes. In other examples, a single lead may include all electrodes 232, 233, 234 along a single axial length of the lead. Processing circuitry 210 also controls stimulation generation circuitry 202 to generate and apply the stimulation signals to selected combinations of electrodes 232, 233, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 233, 234. Such a switch circuit may be a switch array, switch matrix, multiplexer, or any other type of switching circuit configured to selectively couple stimulation energy to selected electrodes 232, 233, 234 and to selectively sense bioelectrical neural signals of a spinal cord of the patient (not shown in FIG. 2) with selected electrodes 232, 233, 234.

In other examples, however, stimulation generation circuitry 202 does not include a switch circuit and switch circuitry 204 does not interface between stimulation generation circuitry 202 and electrodes 232, 233, 234. In these examples, stimulation generation circuitry 202 includes a plurality of pairs of voltage sources, current sources, voltage sinks, or current sinks connected to each of electrodes 232, 233, 234 such that each pair of electrodes has a unique signal circuit. In other words, in these examples, each of electrodes 232, 233, 234 is independently controlled via its own signal circuit (e.g., via a combination of a regulated voltage source and sink or regulated current source and sink), as opposed to switching signals between electrodes 232, 233, 234.

Electrodes 232, 233, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques. In some examples, one or more of electrodes 232, 233, 234 are suitable for sensing the ECAPs. For instance, electrodes 232, 233, 234 may sense the voltage amplitude of a portion of the ECAP signals, where the sensed voltage amplitude, such as the voltage difference between features within the signal, is a characteristic the ECAP signal.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. In the illustrated examples, storage device 212 is also configured to store stimulation parameter settings 242 that define one or more sets of stimulation parameters.

As described, electrodes 232, 233, 234 may be the electrodes that sense the characteristic value of the ECAP signal. Sensor(s) 222 may include one or more accelerometers, optical sensors, chemical sensors, temperature sensors, pressure sensors, or any other types of sensors. Sensor(s) 222 may output patient parameter values that may be used as feedback to control delivery of therapy. For example, sensor(s) 222 may indicate patient activity or posture, and processing circuitry 210 may increase the frequency of control pulses and ECAP sensing in response to detecting increased patient activity or posture.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
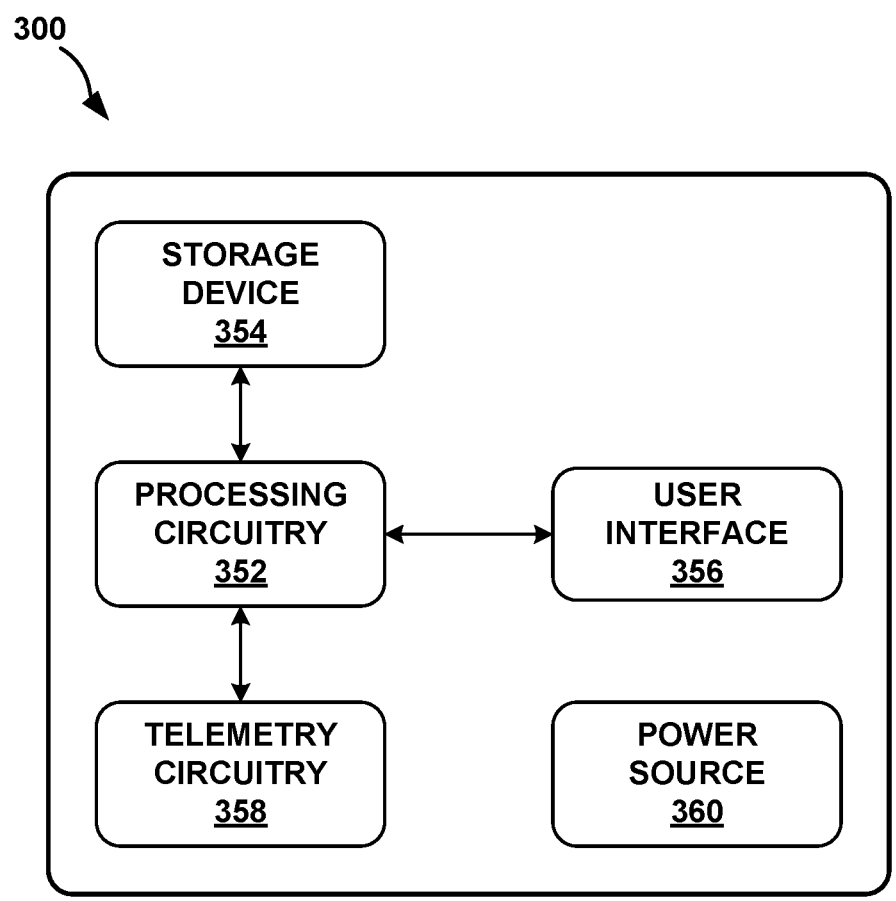
FIG. 3 is a block diagram illustrating an example configuration of components of an example external programmer, in accordance with one or more techniques of this disclosure.

FIG. 3 is a block diagram illustrating an example configuration of components of an example external programmer 300. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode pattern, or receive a user input and send a corresponding command to IMD 200, or instructions for any other functionality. In addition, storage device 354 may include a plurality of programs, where each program includes a parameter set that defines therapy stimulation or control stimulation. Storage device 354 may also store data received from a medical device (e.g., IMD 110). For example, storage device 354 may store ECAP related data recorded at a sensing module of the medical device, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, such as characteristics of ECAP signals and/or ECAP signals resulting from control stimuli provided by IMD 110 as a lead of IMD 110 is moved laterally across the spinal cord of the patient to facilitate identifying the location of the target tissue. In some examples, user interface 356 may co-register fluoroscopy images with the ECAP signals to show, for example ECAP signal amplitude with fluoroscopy image User interface 356 may also receive user input (e.g., indication of when the patient perceives a stimulation pulse) via user interface 356. In some such examples, user interface 356 may provide a series of images to facilitate locating the target tissue. The input may be, for example, in the form of pressing a button on a keypad or selecting an icon from a touch screen. The input may request starting or stopping electrical stimulation, the input may request a new spatial electrode pattern or a change to an existing spatial electrode pattern, of the input may request some other change to the delivery of electrical stimulation. User interface 356 may provide audio and/or visual indicators that are indicative to whether the current position of the lead is more likely to be adjacent to the target tissue that the previous position. For example, as one or more characteristics change to be more indicative of the target tissue (e.g., the latency at the current position is shorter than the latency at the previous position, the peak-to-peak amplitude of the ECAP signal associated with the current position is greater than peak-to-peak amplitude of the ECAP signal associated with the previous position, etc.), user interface 356 may change a color (e.g., red to greed, etc.), change a tone (e.g., lower tone to higher tone, etc.) and/or change a frequency of a tone (e.g., slower to faster, etc.). In some examples, a microphone of external programmer 300 may generate a sound that is related to the characteristics such that the sound is louder when the lead is proximate the implant location. For example, the volume and/or pitch of the audio feedback may be proportional to the peak-to-peak amplitude of the ECAP signal.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

User interface 356 of external programmer 300 may also be configured to receive an indication from a clinician instructing a processor of the medical device to update one or more therapy stimulation programs in response to an indication that the leads have migrated. For example, user interface 356 may receive an indication from the clinician to adjust a pulse width and/or an amplitude of the stimulation parameter values to compensate for the migration of the leads. User interface 356 may also receive instructions from the clinician commanding any electrical stimulation, including therapy stimulation and control stimulation to commence or to cease.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

In some examples, an external device may include functionality attributed to both IMD 200 and external programmer 300. For example, during the interoperative positioning process, the external device may be coupled to the one or more leads 130 in order to deliver stimulus and sense ECAPs in response to each respective stimulus. In addition, the external device may include a user interface that provides, visual, audible, and/or tactile feedback regarding the position of the lead (or electrodes of the lead) to facilitate physician placement of the lead with respect to the anatomy of the patient. In other examples, a fully automated external device may implement the techniques described herein for implanting and positioning lead 130. For example, a surgical robot may implant and place lead 130 according to feedback obtained from the ECAPs as described herein.

Figure 4:
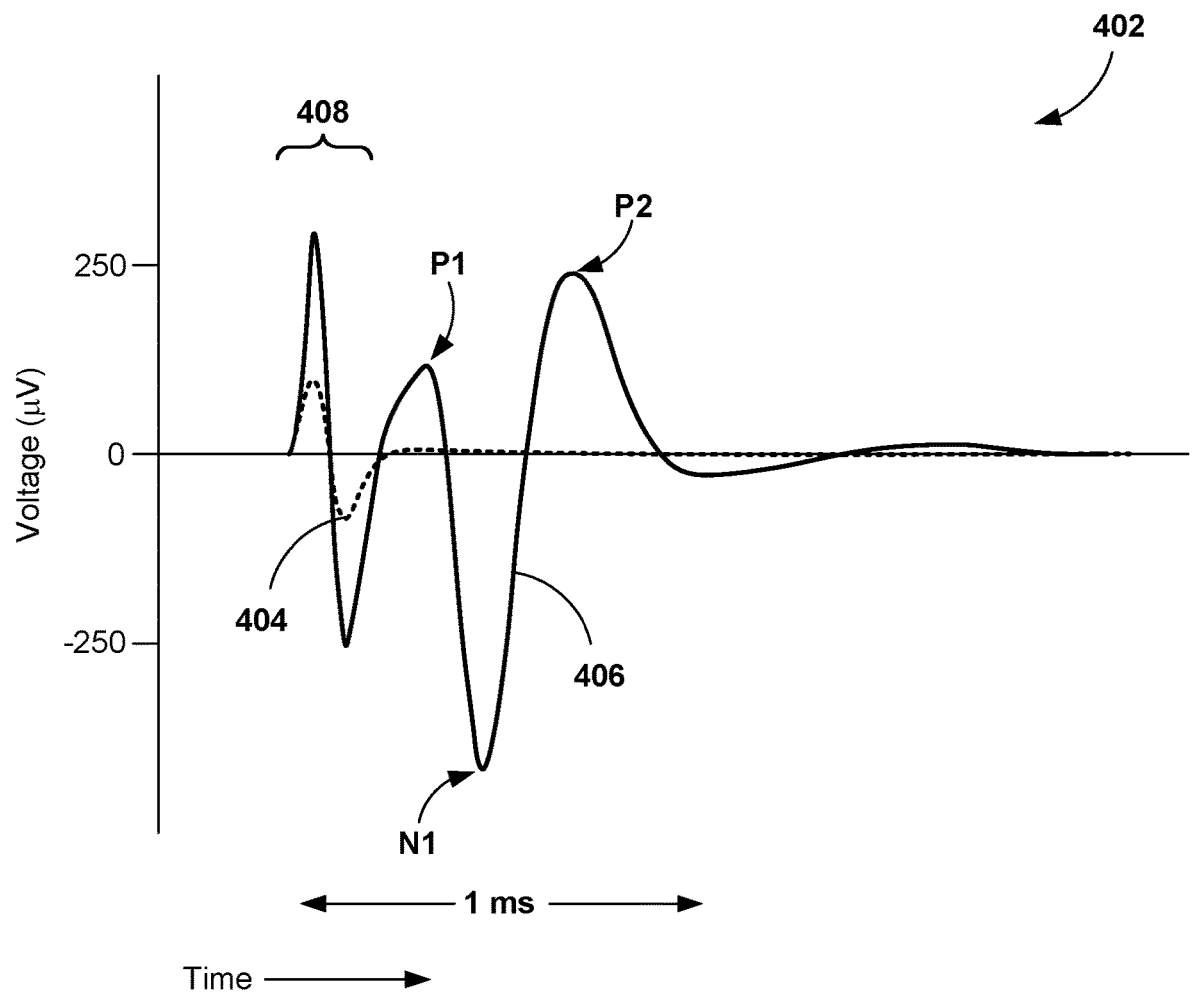
FIG. 4 is a graph of example evoked compound action potentials (ECAPs) sensed for respective stimulation pulses, in accordance with one or more techniques of this disclosure.

FIG. 4 is a graph 402 of example evoked compound action potentials (ECAPs) sensed for respective stimulation pulses, in accordance with one or more techniques of this disclosure. As discussed herein, characteristics of the ECAP signal may be used to determine the location of target tissue when the patient cannot provide feedback. As shown in FIG. 4, graph 402 shows example ECAP signal 404 (dotted line) and ECAP signal 406 (solid line). In some examples, each of ECAP signals 404 and 406 are sensed from control pulses that were delivered from a guarded cathode, where the control pulses are bi-phasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 404 illustrates the voltage amplitude sensed as a result from a sub-detection threshold stimulation pulse. In other words, the stimulation pulse did not elicit a detectable ECAP signal in ECAP signal 404. Peaks 408 of ECAP signal 404 are detected and represent the artifact of the delivered stimulation pulse (e.g., a control pulse that may or may not contribute to a therapeutic effect for the patient). However, no propagating signal is detected after the artifact in ECAP signal 404 because the control pulse was sub-detection threshold.

In contrast to ECAP signal 404, ECAP signal 406 represents the voltage amplitude detected from a supra-detection threshold control pulse. Peaks 408 of ECAP signal 406 are detected and represent the artifact of the delivered control pulse. After peaks 408, ECAP signal 406 also includes peaks P1, N1 (sometime referred to as a valley), and P2, which are three typical peaks representative of propagating action potentials from an ECAP. In the illustrated example, duration of the artifact and peaks P1, N1, and P2 is approximately 1 millisecond (ms). When detecting the ECAP of ECAP signal 406, different characteristics may be identified. For example, the characteristic of the ECAP may be the amplitude between N1 and P2. This N1-P2 amplitude may be easily detectable even if the artifact, a relatively large signal, impinges on P1. Additionally, the N1-P2 amplitude may be minimally affected by electronic drift in the signal. In other examples, the characteristic of the ECAP used to detect the posture state of the patient and/or control informed pulses may be an amplitude of P1, N1, or P2 with respect to neutral or zero voltage. In some examples, the characteristic of the ECAP may be a sum of two or more of peaks P1, N1, or P2. In other examples, the characteristic of ECAP signal 406 may be the area under one or more of peaks P1, N1, and/or P2. In other examples, the characteristic of the ECAP may be a ratio of one of peaks P1, N1, or P2 to another one of the peaks. In some examples, the characteristic of the ECAP is a slope between two or more points in the ECAP signal, such as the slope between N1 and P2. For example, the characteristic may include the difference between two slopes (i.e. slope from N1 to P2 and the slope from P2 to end, etc.). In other examples, the characteristic of the ECAP may be the time between two points of the ECAP, such as the time between N1 and P2. The time between two points in the ECAP signal may be referred to as a latency of the ECAP and may indicate the types of fibers being captured by the control pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples. The amplitude of the ECAP signal generally increases with increased amplitude of the control pulse, as long as the pulse amplitude is greater than threshold such that nerves depolarize and propagate the signal.

Figure 5A:
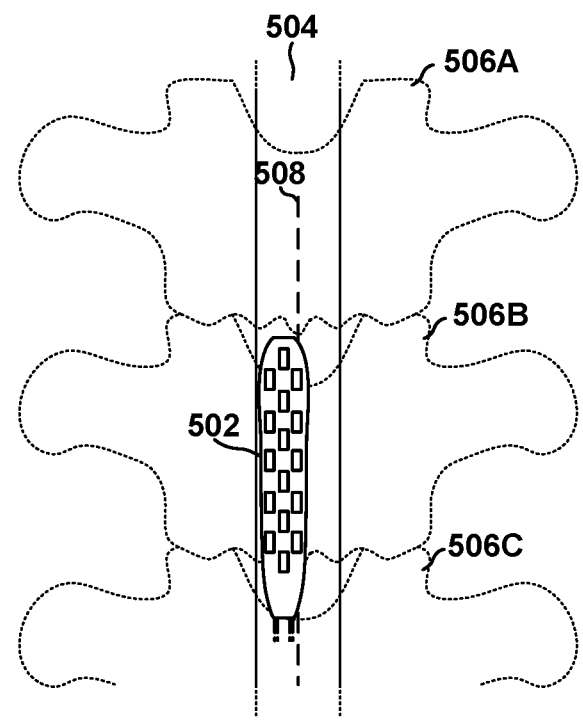
FIGS. 5A, 5B, 5C, 5D, 5E, and 5F illustrate positioning of a paddle lead of an implantable medical device (IMD) adjacent to a spinal cord and the sensed signals from each respective location, in accordance with one or more techniques of this disclosure.
Figure 5B:
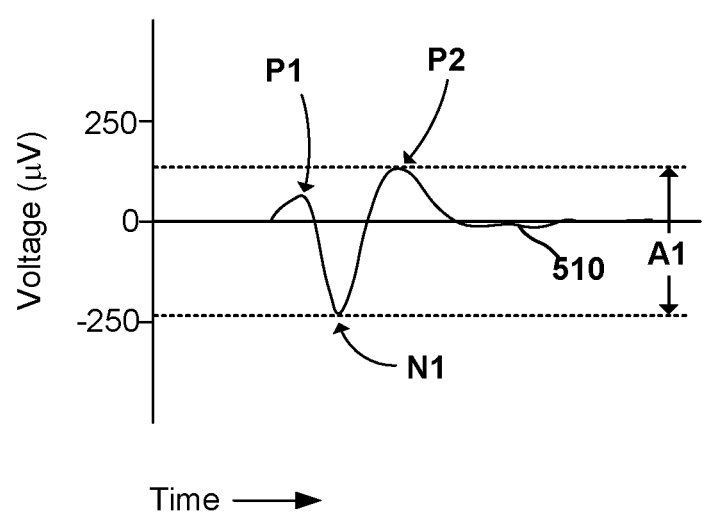
Figure 5C:
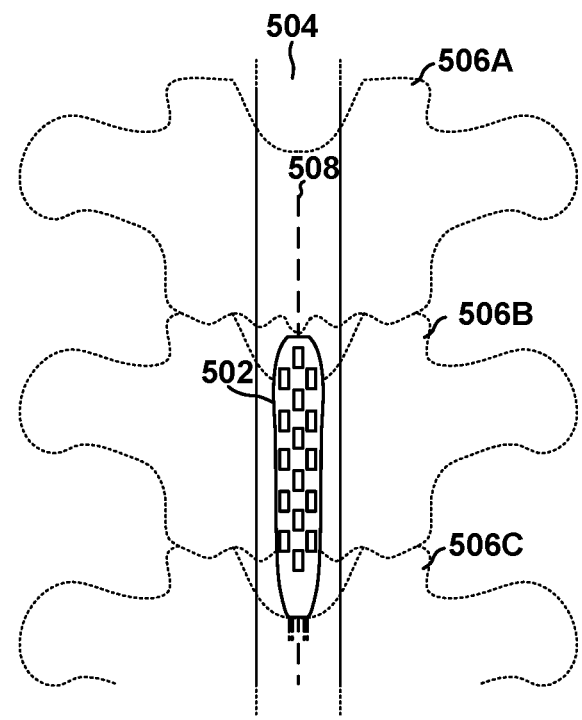
Figure 5D:
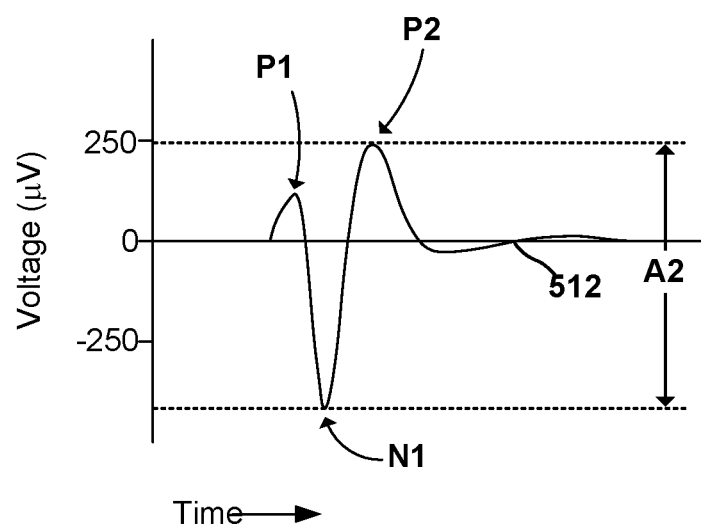
Figure 5E:
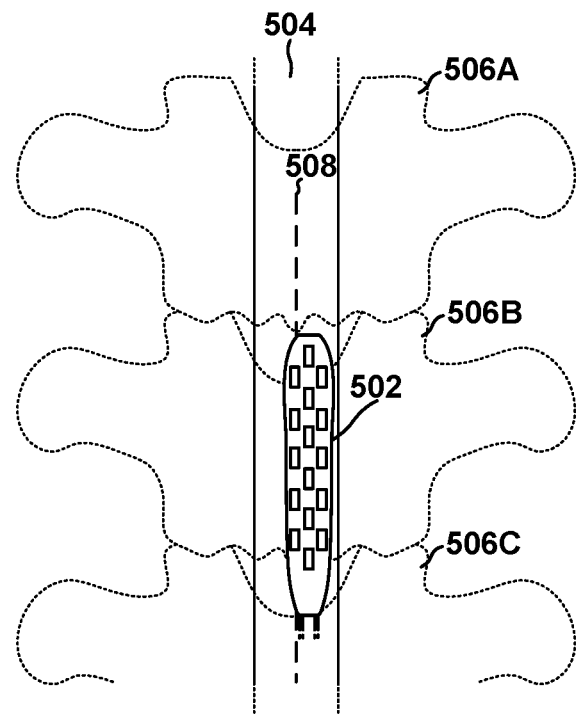
Figure 5F:
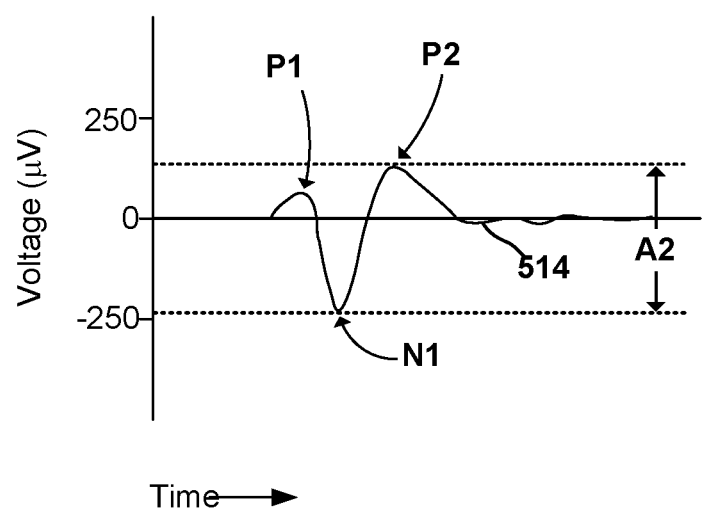

FIGS. 5A, 5C, and 5E illustrate example paddle lead 502 of an implantable medical device (e.g., IMD 110) adjacent to a spinal cord 504 in an epidural space during intraoperative placement, in accordance with one or more techniques of this disclosure. FIGS. 5B, 5D, and 5F illustrated the corresponding ECAP signals. Lead 502 may be an example of lead 130 and lead 230 of FIGS. 1 and 2, respectively. FIGS. 5A, 5C, and 5E illustrated vertebrae 506A, 506B, and 506C (collectively "vertebrae 506") with lamina and transverse processes. For simplicity of illustration, FIGS. 5A, 5C, and 5E do not depict the spinous processes. FIG. 5A illustrates lead 502 in a first position proximate the dura of spinal column 504 on one side of a midline 508. FIG. 5B illustrates an example ECAP signal 510 sensed in response to stimulus at the first location. ECAP signal 510 may be characterized to facilitate comparing ECAP signal 510 to other ECAP signals sensed at other locations. As an example, ECAP signal 510 may be characterized using a characteristic value such as a peak-to-peak amplitude A1 from peak N1 to peak P2 to facilitate feedback to the physician placing lead 502. Any other characteristic value for the ECAP signal 510 may be implemented, such as the area under one or more peaks of ECAP signal 510, amplitudes of three or more peaks, magnitudes of derivatives of ECAP signal 501, etc.

Lead 502 is then moved across spinal column 504 towards midline 508. FIG. 5C illustrates lead 502 in a second position proximate the dura of spinal column 504. In the illustrated example, the second position of lead 502 in FIG.

5C corresponds to midline 508. FIG. 5D illustrates an example ECAP signal 512 sensed in response to stimulus at the second location. While for exemplary purposes, lead 502 is illustrated in the first position in FIG. 5A and in the second position in FIG. 5C, lead 502 may be placed in one more positions between the first position and the second position where an ECAP signal is sensed and characterized. For examples, an ECAP signal may be sensed and characterized every millimeter between the first position and the second position. ECAP signal 512 may be characterized to facilitate comparing ECAP signal 512 to other ECAP signals sensed at other locations. As an example, ECAP signal 512 may be characterized as a peak-to-peak amplitude A2 from peak N1 to peak P2 to facilitate feedback to the physician placing lead 502. For example, A2 of FIG. 5D is greater than A1 of FIG. 5B, which may indicate that the second position for lead 502 of FIG. 5C is closer to the implant location than the first position for lead 502 of FIG. 5A. In other words, the stimulus from lead 502 activated a greater number of nerves which is represented by the greater amplitude A2 as compared with A1 from FIG. 5B.

Lead 502 is then move across spinal column 504 towards the opposite side of midline 508 from the first position as shown in FIG. 5E. FIG. 5E illustrates lead 502 in a third position proximate the dura of spinal column 504. FIG. 5F illustrates an example ECAP signal 514 sensed in response to stimulus at the third location. While for exemplary purposes, lead 502 is illustrated in the second position in FIG. 5C and in the third position in FIG. 5E, lead 502 may be placed in one more positions between the second position and the third position where an ECAP signal is sensed and characterized. For examples, an ECAP signal may be sensed and characterized every millimeter between the second position and the third position. ECAP signal 514 may be characterized to facilitate comparing ECAP signal 514 to other ECAP signals sensed at other locations. As an example, ECAP signal 514 may be characterized as a peak-to-peak amplitude A3 from peak N1 to peak P2 to facilitate feedback to the physician placing lead 502. For example, A2 of FIG. 5D is greater than A3 of FIG. 5F, which may indicate that the second position for lead 502 of FIG. 5C is closer to the implant location than the third position for lead 502 of FIG. 5E. By using this process, a physician or system may determine that the appropriate position for lead 502 corresponds to the greatest amplitude obtained from sensed ECAP signals, such as the second location of FIG. 5C.

Figure 6A:
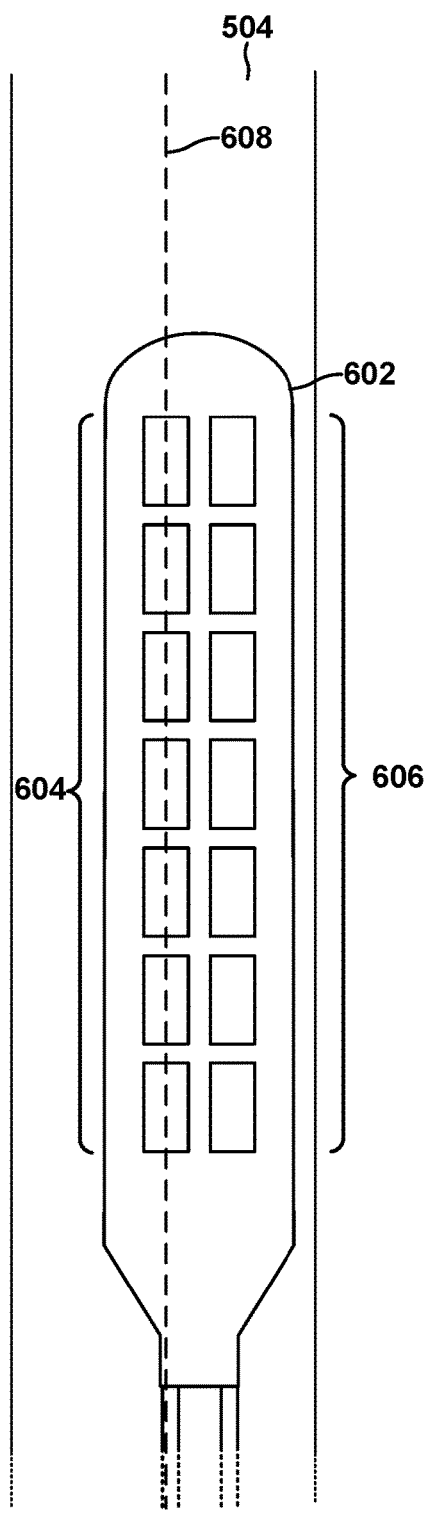
FIGS. 6A and 6B illustrate paddle leads of an implantable medical device (IMD) implanted adjacent to a spinal cord, in accordance with one or more techniques of this disclosure.
Figure 6B:
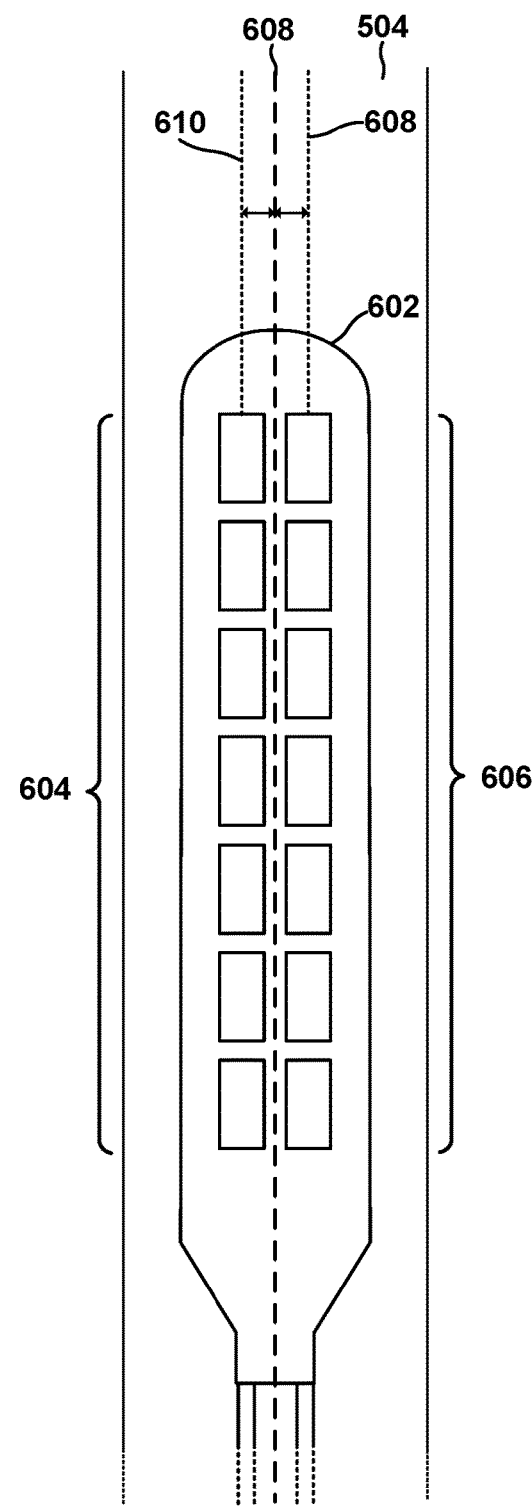

FIGS. 6A and 6B illustrate paddle leads 602 configured to be implanted adjacent to spinal cord 504, in accordance with one or more techniques of this disclosure. In the illustrated examples, paddle leads 602 have an even number of rows (e.g., two rows, etc.) of electrodes 604 and 606. In the illustrated examples, ECAP signals are sensed using one combination of electrodes (e.g., electrodes 604 residing in one column along the axis of lead 602). FIG. 6A illustrates paddle lead 602 locating an implant axis 608 (e.g., an axis that corresponds with the ECAP signal indicative of the implant location, etc.). Electrodes 604 of paddle lead 602 are positioned over implant axis 608 when implant axis 608 is discovered. FIG. 6B illustrates paddle lead 602 in the implant position. Paddle lead 602 is positioned such that central axis 610 and 612 defined by electrodes 604 and 606 respectively are equidistant from an implant axis 608. For example, the system and/or physician may sense ECAPs from electrodes in columns 604 and 606 and determine the appropriate position as shown in FIG. 6B when the ECAPs from respective electrodes 604 and 606 are generally of equal amplitude. In this way, electrodes 604 and 606 may be approximately at equal distances from implant axis 608. In such a manner, a paddle lead with an even number of rows of electrodes may positioned to provide effective therapy to the patient.

Figure 7:
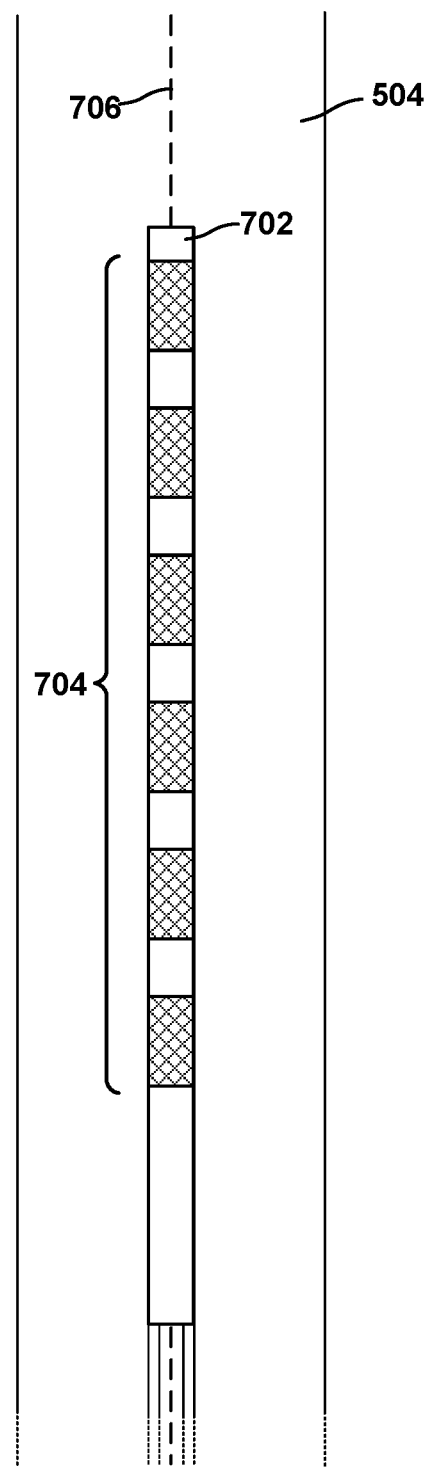
FIG. 7 illustrates an omnidirectional lead of an implantable medical device (IMD) implanted adjacent to a spinal cord, in accordance with one or more techniques of this disclosure

FIG. 7 illustrates an example where lead 702 includes a single row of electrodes 704. As described above, lead 702 is swept from one side of central axis 706 to the other side of central axis 706 to determine, based on an analysis of ECAP signals at each position, a position corresponding to the implant location.

Figure 8:
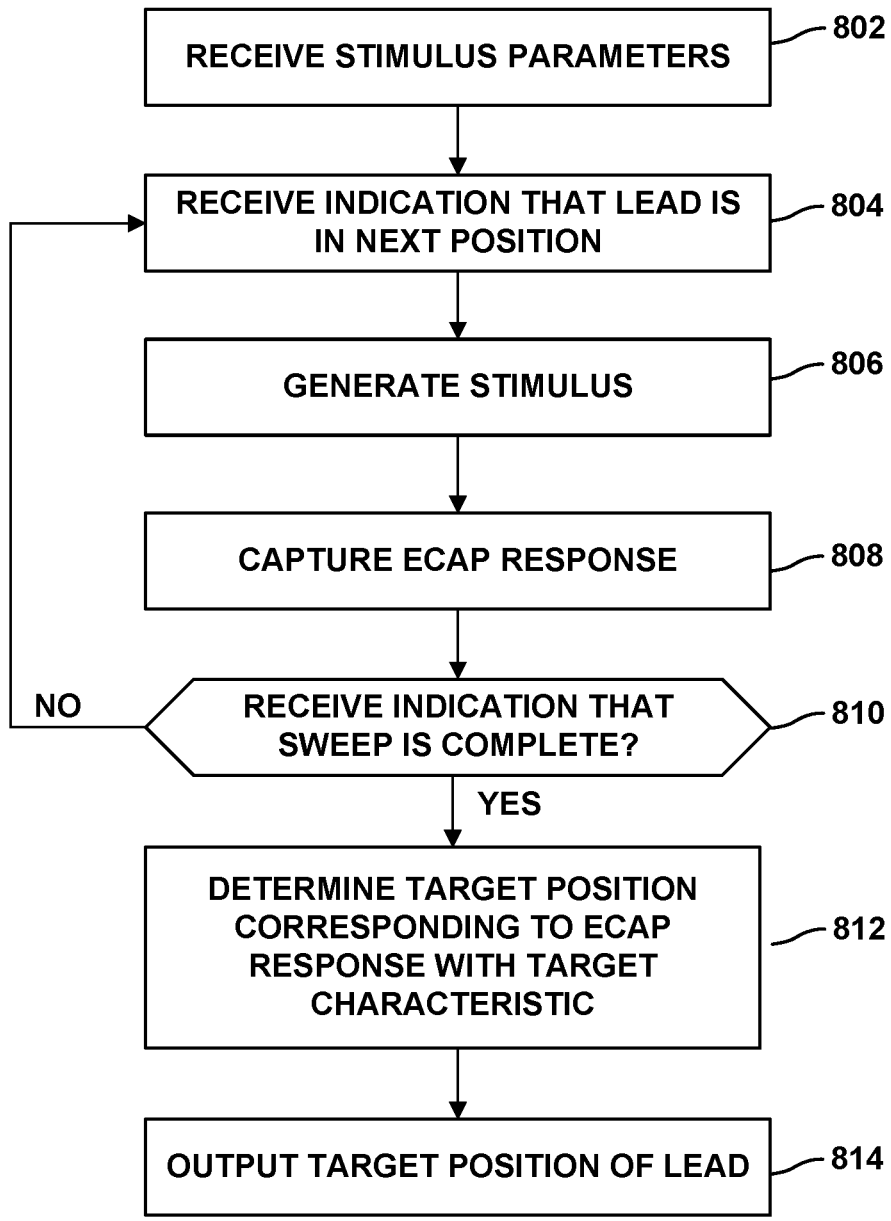
FIG. 8 is a flowchart of an example method to position a lead of an implantable medical device (IMD), in accordance with one or more techniques of this disclosure.

FIG. 8 is a flowchart of an example method to position a lead (e.g., lead 130, 230, 502, 602, 702) of IMD 110, in accordance with one or more techniques of this disclosure. Initially, IMD 110 (e.g., or any other stimulation generation device) receives stimulus parameters to evoke an ECAP signal (802). IMD 110 receives an indication that the lead is in the next (or initial) position (804). For example, a surgeon or instrumentation of a robotic surgery assistant may move the lead into an initial position and provide an indication to IMD 110. IMD 100 then generates a stimulus to evoke the ECAP signal (806). IMD 110 then captures the resultant ECAP signal (808). In some examples, IMD 110 may generate a characteristic value that represents the amplitude of the sensed ECAP signal, such as the peak-to-peak amplitude between N1 and P2. IMD 110 then determines whether it has received an indication that the sweep of lead positions is complete (810). If the sweep is not complete ("NO" at 810), IMD 110 waits until it has received an indication that the lead in in the next position (802).

If the sweep is complete ("YES" at 810), IMD 110 determines a target position (e.g., the implant position) by analyzing the capture ECAP signals and determining which position corresponds to an ECAP signal with a target characteristic (e.g., largest peak-to-peak amplitude, etc.) (812). IMD 110 outputs the target position and/or an identifier associated with an iteration of the sweep to facilitate locating the target position (814). Subsequently, a physician or a robotic surgery assistant may position and install the lead at the target position.

In other examples, the technique of steps 804 through 808 may be repeated until the physician or system confirms that the position is appropriate. Instead of completing a sweep, the system and/or physician may perform steps 804 through 808 iteratively (e.g., moving the lead back and forth) until the system or physician is satisfied with the position. For example, the physician may continue to move the lead in a first direction as the characteristic value of the ECAP signal continues to increase. In response to the characteristic value of the ECAP signal decreasing from the previous characteristic value, the physician can move the lead back to the previous position. A confirmatory ECAP signal can be obtained to determine that the characteristic value does indeed increase again as indicated in that previous position. In this manner, the position of the lead is left at the last position instead of needing to be moved back to the identified position as indicated during a sweep.

In some examples, the system and/or physician may use the techniques described herein to determine if electrodes of the lead are aligned (e.g., approximately parallel) with the spinal cord or other nerve of interest. For example, the system may obtain ECAP signals from electrode combinations at two or more positions along the lead (e.g., at each end of the electrode array). The electrode array may then be iteratively moved to different angular positions with respect to the spinal cord or nerve, and the system may obtain ECAPs from the different electrode combinations at each angular position. The physician or system may determine the appropriate position for the lead (and electrode array) when the characteristic value of the ECAP signals for all electrode combinations are approximately equal (e.g., all electrode combinations sense the greatest amplitude of ECAP characteristic value at that particular angular position). This angular movement process may be performed after the sweep described in FIG. 8 or as part of a combination angular and lateral movement process to identify the appropriate lateral and angular position of the lead with respect to the spinal cord or other nerve.

The following examples are described herein. Example 1: A system includes stimulation circuitry configured to generate electrical stimulation deliverable via an electrode combination of an electrode array; sensing circuitry configured to sense an evoked compound action potential (ECAP) signal; and processing circuitry configured to: control the stimulation circuitry to deliver a first control stimulus to the electrode combination of the electrode array positioned at a first location adjacent to a spinal cord of a patient; receive, from the sensing circuitry, first information representative of a first ECAP signal sensed in response to the first control stimulus; control the stimulation circuitry to deliver a second control stimulus to the electrode combination of the electrode array positioned at a second location adjacent to the spinal cord of the patient; receive, from the sensing circuitry, second information representative of a second ECAP signal in response to the second control stimulus; output a first indication of the first information representative of the first ECAP signal and a second indication of the second information representative of the second ECAP signal.

Example 2: The system of example 1, wherein the processing circuitry is configured to: receive an indication that the electrode array has moved from the first position to the second position; and control the stimulation circuitry to deliver the second control stimulus in response to receiving the indication that the electrode array has moved from the first position to the second position.

Example 3: The system of any of examples 1 or 2, wherein the processing circuitry is configured to: control the stimulation circuitry to deliver a third control stimulus to the electrode combination of the electrode array positioned at a third location adjacent to the spinal cord of the patient; receive, from the sensing circuitry, third information representative of a third ECAP signal in response to the third control stimulus; and output an indication of the third information representative of the third ECAP signal.

Example 4: The system of example 3, wherein the processing circuitry is configured to determine that the second location is a target location based on changes in characteristics between the first information representative of the first ECAP signal and the second information representative of the second ECAP signal and changes in characteristics between the second information representative of the second ECAP signal and the third information representative of the third ECAP signal.

Example 5: The system of example 4, wherein the characteristics includes at least one of a peak-to-peak amplitude, a latency, or an area under a curve.

Example 6: The system of any of examples 1 through 5, wherein when the electrode array is arranged to include an odd number of columns with respect to a lateral axis of the spinal cord, and wherein the processing circuitry is configured to control the stimulation circuitry to deliver the first control stimulus and the second control stimulus to the electrode combination consisting of two or more electrodes disposed in a lateral center column of the electrode array.

Example 7: The system of any of examples 1 through 6, wherein the processing circuitry is configured to control the stimulation circuitry to deliver the first control stimulus and the second control stimulus to the electrode combination consisting of two or more electrodes disposed in a single column adjacent a lateral center of the electrode array arranged to include an even number of columns with respect to a lateral axis of the spinal cord.

Example 8: The system of any of examples 1 through 7, wherein, the processing circuitry is configured to control the stimulation circuitry to deliver the first control stimulus and the second control stimulus to the electrode combination comprising at least one electrode in each of respective different columns of the electrode array arranged to include an even number of columns with respect to a lateral axis of the spinal cord, each of the different columns being adjacent to a lateral center of the electrode array.

Example 9: The system of any of examples 1 through 8, wherein the first indication causes a first visual representation of at least one characteristic within the first information representative of the first ECAP signal to be displayed, and the second indication causes a second visual representation of the at least one characteristic within the second information representative of the second ECAP signal to be displayed, a difference between the first visual representation and the second visual representation corresponding to a difference between the at least one characteristic within the first and second information.

Example 10: The system of any of examples 1 through 9, wherein the first indication causes a first audio representation of at least one characteristic within the first information representative of the first ECAP signal to be produced, and the second indication causes a second audio representation of the at least one characteristic within the second information representative of the second ECAP signal to be produced, a difference between the first audio representation and the second audio representation corresponding to a difference between the at least one characteristic within the first and second information.

Example 11: A method includes receiving, by processing circuitry, first information representative of a first evoked compound action potential (ECAP) signal sensed in response to a first control stimulus delivered to a first location adjacent to a spinal cord of a patient; receiving, by the processing circuitry, second information representative of a second ECAP signal in response to a second control stimulus delivered to a second location adjacent to the spinal cord of the patient; and outputting, by the processing circuitry, a first indication of the first information representative of the first ECAP signal and a second indication of the second information representative of the second ECAP signal.

Example 12: The method of example 11, further including controlling, by the processing circuitry, stimulation circuitry to deliver the first control stimulus; receiving, by the processing circuitry, an indication that the electrode array has moved from the first position to the second position; and controlling, by the processing circuitry, the stimulation circuitry to deliver the second control stimulus in response to receiving the indication that the electrode array has moved from the first position to the second position.

Example 13: The method of example 11, further including receiving, by the processing circuitry, third information representative of a third ECAP signal in response to a third control stimulus delivered to a third location adjacent to the spinal cord of the patient; and outputting, by the processing circuitry, an indication of the third information representative of the third ECAP signal.

Example 14: The method of example 13, comprising determining, by the processing circuitry, that the second location is a target location based on changes in characteristics between the first information representative of the first ECAP signal and the second information representative of the second ECAP signal and changes in characteristics between the second information representative of the second ECAP signal and the third information representative of the third ECAP signal.

Example 15: The method of any of examples 11 through 14, further including controlling, by the processing circuitry, stimulation circuitry to deliver the first control stimulus and the second control stimulus by an electrode array; and when the electrode array is arranged to include an odd number of columns with respect to a lateral axis of the spinal cord, controlling, by the processing circuitry, the stimulation circuitry to deliver the first control stimulus and the second control stimulus to the electrode combination consisting of two or more electrodes disposed in a lateral center column of the electrode array.

Example 16: The method of any of examples 11 through 15, further comprising controlling, by the processing circuitry, stimulation circuitry to deliver the first control stimulus and the second control stimulus by an electrode array; and when the electrode array is arranged to include an even number of columns with respect to a lateral axis of the spinal cord, controlling, by the processing circuitry, the stimulation circuitry to deliver the first control stimulus and the second control stimulus to the electrode combination consisting of two or more electrodes disposed in a single column adjacent a lateral center of the electrode array.

Example 17: The method of any of examples 11 through 16, further comprising controlling, by the processing circuitry, stimulation circuitry to deliver the first control stimulus and the second control stimulus by an electrode array; and when the electrode array is arranged to include an even number of columns with respect to a lateral axis of the spinal cord, controlling, by the processing circuitry, the stimulation circuitry to deliver the first control stimulus and the second control stimulus to the electrode combination comprising at least one electrodes in respective different columns of the electrode array, each of the different columns being adjacent to a lateral center of the electrode array.

Example 18: The method of any of examples 11 through 17, further including displaying a first visual representation of at least one characteristic within the first information representative of the first ECAP signal in response to the first indication; and displaying a second visual representation of the at least one characteristic within the second information representative of the second ECAP signal in response to the second indication, wherein a difference between the first visual representation and the second visual representation corresponding to a difference between the at least one characteristic within the first and second information.

Example 19: The method of any of examples 11 through 18, further including producing a first audio representation of at least one characteristic within the first information representative of the first ECAP signal in response to the first indication; and producing a second audio representation of the at least one characteristic within the second information representative of the second ECAP signal in response to the second indication, wherein a difference between the first audio representation and the second audio representation corresponding to a difference between the at least one characteristic within the first and second information.

Example 20: A computer readable medium comprising instructions that, when executed, cause processing circuitry to: receive a first input that an electrode array has been positioned in a first location adjacent to a spinal cord of a patient; control stimulation circuitry to deliver a first control stimulus to an electrode combination of the electrode array; receive, from the sensing circuitry, first information representative of a first evoked compound action potential (ECAP) signal sensed in response to the first control stimulus; receive a second input that the electrode array has moved from the first location to a second location adjacent to the spinal cord of the patient; control the stimulation circuitry to deliver a second control stimulus to the electrode combination of the electrode array positioned at the second location; receive, from the sensing circuitry, second information representative of a second ECAP signal in response to the second control stimulus; output a first indication of the first information representative of the first ECAP signal and a second indication of the second information representative of the second ECAP signal.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:
stimulation circuitry configured to generate electrical stimulation deliverable via an electrode combination of an electrode array during an implantation placement procedure;
sensing circuitry configured to sense an evoked compound action potential (ECAP) signal; and
processing circuitry configured to:
control the stimulation circuitry to deliver a first control stimulus to the electrode combination of the electrode array positioned at a first potential implant location adjacent to a spinal cord of a patient;
receive, from the sensing circuitry, first information representative of a first ECAP signal sensed in response to the first control stimulus;
control the stimulation circuitry to deliver a second control stimulus to the electrode combination of the electrode array positioned at a second potential implant location different from the first potential implant location and adjacent to the spinal cord of the patient;
receive, from the sensing circuitry, second information representative of a second ECAP signal in response to the second control stimulus;
determine a first latency of the first ECAP signal and a second latency of the second ECAP signal;
determine one of the first latency of the first ECAP signal or the second latency of the second ECAP signal having a lowest latency;
select, according to the lowest latency, one of the first potential implant location associated with the first ECAP signal or the second potential implant location associated with the second ECAP signal as a target position for implantation of the electrode array; and
output an indication of the target position.

2. The system of claim 1, wherein the processing circuitry is configured to:
receive an indication that the electrode array has moved from the first position to the second position; and
control the stimulation circuitry to deliver the second control stimulus in response to receiving the indication that the electrode array has moved from the first position to the second position.

3. The system of claim 1, wherein the processing circuitry is configured to:
control the stimulation circuitry to deliver a third control stimulus to the electrode combination of the electrode array positioned at a third location adjacent to the spinal cord of the patient;
receive, from the sensing circuitry, third information representative of a third ECAP signal in response to the third control stimulus; and
output an indication of the third information representative of the third ECAP signal.

4. The system of claim 3, wherein the processing circuitry is configured to determine that the second location is a target location based on changes in characteristics between the first information representative of the first ECAP signal and the second information representative of the second ECAP signal and changes in characteristics between the second information representative of the second ECAP signal and the third information representative of the third ECAP signal.

5. The system of claim 4, wherein the characteristics includes at least one of a peak-to-peak amplitude, a latency, or an area under a curve.

6. The system of claim 1, wherein when the electrode array is arranged to include an odd number of columns with respect to a lateral axis of the spinal cord, and wherein the processing circuitry is configured to control the stimulation circuitry to deliver the first control stimulus and the second control stimulus to the electrode combination consisting of two or more electrodes disposed in a lateral center column of the electrode array.

7. The system of claim 1, wherein the processing circuitry is configured to control the stimulation circuitry to deliver the first control stimulus and the second control stimulus to the electrode combination consisting of two or more electrodes disposed in a single column adjacent a lateral center of the electrode array arranged to include an even number of columns with respect to a lateral axis of the spinal cord.

8. The system of claim 1, wherein, the processing circuitry is configured to control the stimulation circuitry to deliver the first control stimulus and the second control stimulus to the electrode combination comprising at least one electrode in each of respective different columns of the electrode array arranged to include an even number of columns with respect to a lateral axis of the spinal cord, each of the different columns being adjacent to a lateral center of the electrode array.

9. The system of claim 1, wherein the processing circuitry is configured to:
output, for display, a first visual representation of at least one characteristic within the first information representative of the first ECAP signal to be displayed, and
output, for display, a second visual representation of the at least one characteristic within the second information representative of the second ECAP signal to be displayed, a difference between the first visual representation and the second visual representation corresponding to a difference between the at least one characteristic within the first and second information.

10. The system of claim 1, wherein the processing circuitry is configured to:
output, for presentation, a first audio representation of at least one characteristic within the first information representative of the first ECAP signal to be produced, and
output, for presentation, a second audio representation of the at least one characteristic within the second information representative of the second ECAP signal to be produced, a difference between the first audio representation and the second audio representation corresponding to a difference between the at least one characteristic within the first and second information.

11. The system of claim 1, wherein the second location is at least lateral from the first location.

12. A method comprising:
receiving, by processing circuitry, first information representative of a first evoked compound action potential (ECAP) signal sensed in response to a first control stimulus delivered to a first potential implant location adjacent to a spinal cord of a patient during an implantation placement procedure;
receiving, by the processing circuitry, second information representative of a second ECAP signal in response to a second control stimulus delivered to a second potential implant location different from the first potential implant location and adjacent to the spinal cord of the patient during the implantation placement procedure;
determining, by the processing circuitry, a first latency of the first ECAP signal and a second latency of the second ECAP signal;

determining, by the processing circuitry, one of the first latency of the first ECAP signal or the second latency of the second ECAP signal having a lowest latency;
selecting, by the processing circuitry and according to the lowest latency, one of the first potential implant location associated with the first ECAP signal or the second potential implant location associated with the second ECAP signal as a target position for implantation of the electrode array; and
outputting, by the processing circuitry, an indication of the target position.

13. The method of claim 12, further comprising:
controlling, by the processing circuitry, stimulation circuitry to deliver the first control stimulus;
receiving, by the processing circuitry, an indication that the electrode array has moved from the first position to the second position; and
controlling, by the processing circuitry, the stimulation circuitry to deliver the second control stimulus in response to receiving the indication that the electrode array has moved from the first position to the second position.

14. The method of claim 12, further comprising:
receiving, by the processing circuitry, third information representative of a third ECAP signal in response to a third control stimulus delivered to a third location adjacent to the spinal cord of the patient; and
outputting, by the processing circuitry, an indication of the third information representative of the third ECAP signal.

15. The method of claim 14, further comprising determining, by the processing circuitry, that the second location is a target location based on changes in characteristics between the first information representative of the first ECAP signal and the second information representative of the second ECAP signal and changes in characteristics between the second information representative of the second ECAP signal and the third information representative of the third ECAP signal.

16. The method of claim 12, further comprising:
controlling, by the processing circuitry, stimulation circuitry to deliver the first control stimulus and the second control stimulus by an electrode array; and
when the electrode array is arranged to include an odd number of columns with respect to a lateral axis of the spinal cord, controlling, by the processing circuitry, the stimulation circuitry to deliver the first control stimulus and the second control stimulus to the electrode combination consisting of two or more electrodes disposed in a lateral center column of the electrode array.

17. The method of claim 12, further comprising:
controlling, by the processing circuitry, stimulation circuitry to deliver the first control stimulus and the second control stimulus by an electrode array; and
when the electrode array is arranged to include an even number of columns with respect to a lateral axis of the spinal cord, controlling, by the processing circuitry, the stimulation circuitry to deliver the first control stimulus and the second control stimulus to the electrode combination consisting of two or more electrodes disposed in a single column adjacent a lateral center of the electrode array.

18. The method of claim 12, further comprising:
controlling, by the processing circuitry, stimulation circuitry to deliver the first control stimulus and the second control stimulus by an electrode array; and when the electrode array is arranged to include an even number of columns with respect to a lateral axis of the spinal cord, controlling, by the processing circuitry, the stimulation circuitry to deliver the first control stimulus and the second control stimulus to the electrode combination comprising at least one electrodes in respective different columns of the electrode array, each of the different columns being adjacent to a lateral center of the electrode array.

19. The method of claim 12, further comprising:
displaying a first visual representation of at least one characteristic within the first information representative of the first ECAP signal; and
displaying a second visual representation of the at least one characteristic within the second information representative of the second ECAP signal, wherein a difference between the first visual representation and the second visual representation corresponding to a difference between the at least one characteristic within the first and second information.

20. The method of claim 12, further comprising:
producing a first audio representation of at least one characteristic within the first information representative of the first ECAP signal; and
producing a second audio representation of the at least one characteristic within the second information representative of the second ECAP signal, wherein a difference between the first audio representation and the second audio representation corresponding to a difference between the at least one characteristic within the first and second information.

21. A computer readable medium comprising instructions that, when executed, cause processing circuitry to:
receive a first input that an electrode array has been positioned in a first potential implant location adjacent to a spinal cord of a patient during an implantation placement procedure;
control stimulation circuitry to deliver a first control stimulus to an electrode combination of the electrode array;
receive, from the sensing circuitry, first information representative of a first evoked compound action potential (ECAP) signal sensed in response to the first control stimulus;
receive a second input that the electrode array has moved from the first potential implant location to a second potential implant location different from the first location and adjacent to the spinal cord of the patient during the implantation placement procedure;
control the stimulation circuitry to deliver a second control stimulus to the electrode combination of the electrode array positioned at the second location;
receive, from the sensing circuitry, second information representative of a second ECAP signal in response to the second control stimulus;
determine a first latency of the first ECAP signal and a second latency of the second ECAP signal;
determine one of the first latency of the first ECAP signal or the second latency of the second ECAP signal having a lowest latency;
select, according to the lowest latency, one of the first potential implant location associated with the first ECAP signal or the second potential implant location associated with the second ECAP signal as a target position for implantation of the electrode array; and output an indication of the target position.

* * * * *